US012064130B2

(12) United States Patent
O'Malley et al.

(10) Patent No.: US 12,064,130 B2
(45) Date of Patent: Aug. 20, 2024

(54) VASCULAR OBSTRUCTION RETRIEVAL DEVICE HAVING SLIDING CAGES PINCH MECHANISM

(71) Applicant: Neuravi Limited, Galway (IE)

(72) Inventors: Thomas O'Malley, Westport (IE); Stephen Whelan, Galway (IE)

(73) Assignee: Neuravi Limited, Galway (IE)

( * ) Notice: Subject to any disclaimer, the term of this patent is extended or adjusted under 35 U.S.C. 154(b) by 99 days.

(21) Appl. No.: 17/205,179

(22) Filed: Mar. 18, 2021

(65) Prior Publication Data

US 2022/0296262 A1  Sep. 22, 2022

(51) Int. Cl.
*A61B 17/221* (2006.01)
*A61B 17/00* (2006.01)

(52) U.S. Cl.
CPC .. *A61B 17/221* (2013.01); *A61B 2017/00367* (2013.01); *A61B 2017/00862* (2013.01); *A61B 2017/00867* (2013.01)

(58) Field of Classification Search
CPC ........ A61B 17/221; A61B 2017/00367; A61B 2017/00862; A61B 2017/00867; A61B 2218/001; A61F 2/01; A61F 2/0108; F61F 2/012
See application file for complete search history.

(56) References Cited

U.S. PATENT DOCUMENTS

| | | | |
|---|---|---|---|
| 2,828,147 A | 12/1899 | Peiffer | |
| 3,361,460 A | 1/1968 | Gerhart et al. | |
| 4,455,717 A | 6/1984 | Gray | |
| 4,611,594 A | 9/1986 | Grayhack et al. | |
| 4,612,931 A | 9/1986 | Dormia | |
| 4,643,184 A | 2/1987 | Mobin-Uddin | |
| 4,727,873 A | 3/1988 | Mobin-Uddin | |

(Continued)

FOREIGN PATENT DOCUMENTS

| | | |
|---|---|---|
| CN | 2557083 Y | 6/2003 |
| CN | 101172051 A | 5/2008 |

(Continued)

OTHER PUBLICATIONS

US 6,348,062 B1, 02/2002, Hopkins et al. (withdrawn)
Extended European Search Report issued in European Patent Application No. 22 16 2599 dated Aug. 2, 2022.

*Primary Examiner* — Sarah A Long
*Assistant Examiner* — James R McGinnity
(74) *Attorney, Agent, or Firm* — Troutman Pepper Hamilton Sanders LLP

(57) ABSTRACT

The disclosed technology includes a clot retrieval device being configured to retrieve a clot from a blood vessel and having a constrained delivery configuration and a clot engaging configuration. The device can include a first expandable framework having a first plurality of struts that form a first body and a second expandable framework having a second plurality of struts that form a second body upon the clot retrieval device transitioning from the constrained delivery configuration to the clot engaging configuration. In the clot engaging configuration, the first body can be configured to move from a first position to a second position in relation to the second body. Upon moving from the first position to the second position, the clot retrieval device can pinch the clot between the first body and the second body.

18 Claims, 7 Drawing Sheets

(56) References Cited

U.S. PATENT DOCUMENTS

| | | |
|---|---|---|
| 4,793,348 A | 12/1988 | Palmaz |
| 4,873,978 A | 10/1989 | Ginsburg |
| 5,011,488 A | 4/1991 | Ginsburg |
| 5,084,065 A | 1/1992 | David et al. |
| 5,092,839 A | 3/1992 | Kipperman |
| 5,100,423 A | 3/1992 | Fearnot |
| 5,102,415 A | 4/1992 | Guenther et al. |
| 5,108,419 A | 4/1992 | Reger et al. |
| 5,122,136 A | 6/1992 | Guglielmi et al. |
| 5,163,951 A | 11/1992 | Pinchuk et al. |
| 5,171,233 A | 12/1992 | Amplatz et al. |
| 5,171,259 A | 12/1992 | Inoue |
| 5,217,441 A | 6/1993 | Shichman |
| 5,234,437 A | 8/1993 | Sepetka |
| 5,236,447 A | 8/1993 | Kubo et al. |
| 5,330,482 A | 7/1994 | Gibbs et al. |
| 5,383,887 A | 1/1995 | Nadal |
| 5,387,219 A | 2/1995 | Rappe |
| 5,387,226 A | 2/1995 | Miraki |
| 5,449,372 A | 9/1995 | Schmaltz et al. |
| 5,499,985 A | 3/1996 | Hein et al. |
| 5,538,512 A | 7/1996 | Zenzon et al. |
| 5,538,515 A | 7/1996 | Kafry et al. |
| 5,549,626 A | 8/1996 | Miller et al. |
| 5,558,652 A | 9/1996 | Henke |
| 5,609,627 A | 3/1997 | Goicoechea et al. |
| 5,624,461 A | 4/1997 | Mariant |
| 5,639,277 A | 6/1997 | Mariant et al. |
| 5,639,278 A | 6/1997 | Dereume et al. |
| 5,645,558 A | 7/1997 | Horton |
| 5,653,605 A | 8/1997 | Woehl et al. |
| 5,658,296 A | 8/1997 | Bates et al. |
| 5,665,117 A | 9/1997 | Rhodes |
| 5,695,519 A | 12/1997 | Summers et al. |
| 5,709,704 A | 1/1998 | Nott et al. |
| 5,713,853 A | 2/1998 | Clark et al. |
| 5,733,325 A | 3/1998 | Robinson et al. |
| 5,769,871 A | 6/1998 | Mers Kelly et al. |
| 5,769,884 A | 6/1998 | Solovay |
| 5,779,686 A | 7/1998 | Sato et al. |
| 5,779,716 A | 7/1998 | Cano et al. |
| 5,800,519 A | 9/1998 | Sandock |
| 5,810,874 A | 9/1998 | Lefebvre |
| 5,814,064 A | 9/1998 | Daniel et al. |
| 5,824,041 A | 10/1998 | Lenker et al. |
| 5,827,304 A | 10/1998 | Hart |
| 5,853,422 A | 12/1998 | Huebsch et al. |
| 5,855,598 A | 1/1999 | Pinchuk |
| 5,893,869 A | 4/1999 | Barnhart et al. |
| 5,895,398 A | 4/1999 | Wensel et al. |
| 5,897,567 A | 4/1999 | Ressemann et al. |
| 5,904,698 A | 5/1999 | Thomas et al. |
| 5,911,702 A | 6/1999 | Romley et al. |
| 5,911,725 A | 6/1999 | Boury |
| 5,919,126 A | 7/1999 | Armini |
| 5,931,509 A | 8/1999 | Bartholomew |
| 5,935,139 A | 8/1999 | Bates |
| 5,947,995 A | 9/1999 | Samuels |
| 6,063,113 A | 5/2000 | Kavteladze et al. |
| 6,066,149 A | 5/2000 | Samson et al. |
| 6,066,158 A | 5/2000 | Engelson et al. |
| 6,093,196 A | 7/2000 | Okada |
| 6,093,199 A | 7/2000 | Brown et al. |
| 6,096,053 A | 8/2000 | Bates |
| 6,099,534 A | 8/2000 | Bates et al. |
| 6,099,559 A | 8/2000 | Nolting |
| 6,102,932 A | 8/2000 | Kurz |
| 6,106,548 A | 8/2000 | Roubin et al. |
| 6,129,739 A | 10/2000 | Khosravi |
| 6,143,022 A | 11/2000 | Shull et al. |
| 6,146,404 A | 11/2000 | Kim et al. |
| 6,156,064 A | 12/2000 | Chouinard |
| 6,165,194 A | 12/2000 | Denardo |
| 6,165,199 A | 12/2000 | Barbut |
| 6,168,604 B1 | 1/2001 | Cano |
| 6,168,622 B1 | 1/2001 | Mazzocchi |
| 6,174,318 B1 | 1/2001 | Bates et al. |
| 6,179,861 B1 | 1/2001 | Khosravi et al. |
| 6,203,561 B1 | 3/2001 | Ramee et al. |
| 6,214,026 B1 | 4/2001 | Lepak et al. |
| 6,221,006 B1 | 4/2001 | Dubrul et al. |
| 6,221,096 B1 | 4/2001 | Aiba et al. |
| 6,231,597 B1 | 5/2001 | Deem et al. |
| 6,238,412 B1 | 5/2001 | Dubrul et al. |
| 6,245,012 B1 | 6/2001 | Kleshinski |
| 6,245,087 B1 | 6/2001 | Addis |
| 6,251,122 B1 | 6/2001 | Tsukernik |
| 6,254,571 B1 | 7/2001 | Hart |
| 6,264,663 B1 | 7/2001 | Cano |
| 6,267,777 B1 | 7/2001 | Bosma et al. |
| 6,290,710 B1 | 9/2001 | Cryer et al. |
| 6,312,444 B1 | 11/2001 | Barbut |
| 6,315,778 B1 | 11/2001 | Gambale et al. |
| 6,325,815 B1 | 12/2001 | Kusleika et al. |
| 6,325,819 B1 | 12/2001 | Pavcnik et al. |
| 6,334,864 B1 | 1/2002 | Amplatz et al. |
| 6,336,934 B1 | 1/2002 | Gilson et al. |
| 6,346,116 B1 | 2/2002 | Brooks et al. |
| 6,348,056 B1 | 2/2002 | Bates et al. |
| 6,350,271 B1 | 2/2002 | Kurz et al. |
| 6,355,057 B1 | 3/2002 | DeMarais et al. |
| 6,361,545 B1 | 3/2002 | Macoviak et al. |
| 6,364,895 B1 | 4/2002 | Greenhalgh |
| 6,375,668 B1 | 4/2002 | Gifford et al. |
| 6,375,670 B1 | 4/2002 | Greenhalgh |
| 6,383,205 B1 | 5/2002 | Samson et al. |
| 6,383,206 B1 | 5/2002 | Gillick et al. |
| 6,391,037 B1 | 5/2002 | Greenhalgh |
| 6,402,771 B1 | 6/2002 | Palmer et al. |
| 6,416,541 B2 | 7/2002 | Denardo |
| 6,425,909 B1 | 7/2002 | Dieck et al. |
| 6,428,558 B1 | 8/2002 | Jones et al. |
| 6,432,122 B1 | 8/2002 | Gilson et al. |
| 6,436,112 B2 | 8/2002 | Wensel et al. |
| 6,458,139 B1 | 10/2002 | Palmer et al. |
| 6,485,497 B2 | 11/2002 | Wensel et al. |
| 6,485,501 B1 | 11/2002 | Green |
| 6,485,502 B2 | 11/2002 | Don Michael et al. |
| 6,488,701 B1 | 12/2002 | Nolting et al. |
| 6,511,492 B1 | 1/2003 | Rosenbluth et al. |
| 6,530,935 B2 | 3/2003 | Wensel et al. |
| 6,530,939 B1 | 3/2003 | Hopkins et al. |
| 6,540,768 B1 | 4/2003 | Diaz et al. |
| 6,544,279 B1 | 4/2003 | Hopkins et al. |
| 6,551,341 B2 | 4/2003 | Boylan et al. |
| 6,551,342 B1 | 4/2003 | Shen et al. |
| 6,575,996 B1 | 6/2003 | Denison et al. |
| 6,575,997 B1 | 6/2003 | Palmer et al. |
| 6,582,448 B1 | 6/2003 | Boyle et al. |
| 6,585,756 B1 | 7/2003 | Strecker |
| 6,589,265 B1 | 7/2003 | Palmer et al. |
| 6,592,607 B1 | 7/2003 | Palmer et al. |
| 6,592,614 B2 | 7/2003 | Lenker et al. |
| 6,592,616 B1 | 7/2003 | Stack et al. |
| 6,598,265 B2 | 7/2003 | Lee |
| 6,602,265 B2 | 8/2003 | Dubrul et al. |
| 6,602,271 B2 | 8/2003 | Adams et al. |
| 6,602,272 B2 | 8/2003 | Boylan et al. |
| 6,605,102 B1 | 8/2003 | Mazzocchi et al. |
| 6,610,077 B1 | 8/2003 | Hancock et al. |
| 6,616,679 B1 | 9/2003 | Khosravi et al. |
| 6,632,241 B1 | 10/2003 | Hancock et al. |
| 6,638,245 B2 | 10/2003 | Miller et al. |
| 6,638,293 B1 | 10/2003 | Makower et al. |
| 6,641,590 B1 | 11/2003 | Palmer et al. |
| 6,656,218 B1 | 12/2003 | Denardo et al. |
| 6,660,021 B1 | 12/2003 | Palmer et al. |
| 6,663,650 B2 | 12/2003 | Sepetka et al. |
| 6,673,089 B1 | 1/2004 | Yassour et al. |
| 6,685,722 B1 | 2/2004 | Rosenbluth et al. |
| 6,692,504 B2 | 2/2004 | Kurz et al. |
| 6,692,508 B2 | 2/2004 | Wensel et al. |
| 6,692,509 B2 | 2/2004 | Wensel et al. |
| 6,695,858 B1 | 2/2004 | Dubrul et al. |

(56) References Cited

U.S. PATENT DOCUMENTS

| | | |
|---|---|---|
| 6,702,782 B2 | 3/2004 | Miller et al. |
| 6,702,834 B1 | 3/2004 | Boylan et al. |
| 6,709,465 B2 | 3/2004 | Mitchell et al. |
| 6,712,834 B2 | 3/2004 | Yassour et al. |
| 6,726,701 B2 | 4/2004 | Gilson et al. |
| 6,726,703 B2 | 4/2004 | Broome et al. |
| 6,730,104 B1 | 5/2004 | Sepetka et al. |
| 6,783,528 B2 | 8/2004 | Vincent-Prestigiacomo |
| 6,783,538 B2 | 8/2004 | McGuckin, Jr. et al. |
| 6,824,545 B2 | 11/2004 | Sepetka et al. |
| 6,855,155 B2 | 2/2005 | Denardo et al. |
| 6,878,163 B2 | 4/2005 | Denardo et al. |
| 6,890,340 B2 | 5/2005 | Duane |
| 6,913,612 B2 | 7/2005 | Palmer et al. |
| 6,913,618 B2 | 7/2005 | Denardo et al. |
| 6,939,361 B1 | 9/2005 | Kleshinski |
| 6,953,472 B2 | 10/2005 | Palmer et al. |
| 6,989,019 B2 | 1/2006 | Mazzocchi et al. |
| 6,989,021 B2 | 1/2006 | Bosma et al. |
| 6,994,718 B2 | 2/2006 | Groothuis et al. |
| 7,004,954 B1 | 2/2006 | Voss et al. |
| 7,004,955 B2 | 2/2006 | Shen et al. |
| 7,004,956 B2 | 2/2006 | Palmer et al. |
| 7,008,434 B2 | 3/2006 | Kurz et al. |
| 7,033,376 B2 | 4/2006 | Tsukernik |
| 7,041,116 B2 | 5/2006 | Goto et al. |
| 7,048,758 B2 | 5/2006 | Boyle et al. |
| 7,052,500 B2 | 5/2006 | Bashiri et al. |
| 7,058,456 B2 | 6/2006 | Pierce |
| 7,063,707 B2 | 6/2006 | Bose et al. |
| 7,083,633 B2 | 8/2006 | Morrill et al. |
| 7,083,822 B2 | 8/2006 | Brightbill |
| 7,094,249 B1 | 8/2006 | Broome et al. |
| 7,097,653 B2 | 8/2006 | Freudenthal et al. |
| 7,101,380 B2 | 9/2006 | Khachin et al. |
| 7,172,614 B2 | 2/2007 | Boyle et al. |
| 7,175,655 B1 | 2/2007 | Molaei |
| 7,179,273 B1 | 2/2007 | Palmer et al. |
| 7,185,922 B2 | 3/2007 | Takayanagi et al. |
| 7,220,271 B2 | 5/2007 | Clubb et al. |
| 7,226,464 B2 | 6/2007 | Garner et al. |
| 7,229,472 B2 | 6/2007 | DePalma et al. |
| 7,241,304 B2 | 7/2007 | Boyle et al. |
| 7,241,308 B2 | 7/2007 | Andreas et al. |
| 7,288,112 B2 | 10/2007 | Denardo et al. |
| 7,300,458 B2 | 11/2007 | Henkes et al. |
| 7,306,618 B2 | 12/2007 | Demond et al. |
| 7,314,483 B2 | 1/2008 | Andau et al. |
| 7,316,692 B2 | 1/2008 | Huffmaster |
| 7,323,001 B2 | 1/2008 | Clubb et al. |
| 7,331,976 B2 | 2/2008 | McGuckin, Jr. et al. |
| 7,344,550 B2 | 3/2008 | Carrison et al. |
| 7,399,308 B2 | 7/2008 | Borillo et al. |
| 7,410,491 B2 | 8/2008 | Hopkins et al. |
| 7,425,215 B2 | 9/2008 | Boyle et al. |
| 7,452,496 B2 | 11/2008 | Brady et al. |
| 7,491,215 B2 | 2/2009 | Vale et al. |
| 7,491,216 B2 | 2/2009 | Brady |
| 7,510,565 B2 | 3/2009 | Gilson et al. |
| 7,534,252 B2 | 5/2009 | Sepetka et al. |
| 7,556,636 B2 | 7/2009 | Mazzocchi et al. |
| 7,582,111 B2 | 9/2009 | Krolik et al. |
| 7,594,926 B2 | 9/2009 | Linder et al. |
| 7,604,649 B2 | 10/2009 | McGuckin, Jr. et al. |
| 7,604,650 B2 | 10/2009 | Bergheim |
| 7,609,649 B1 | 10/2009 | Bhandari et al. |
| 7,618,434 B2 | 11/2009 | Santra et al. |
| 7,662,165 B2 | 2/2010 | Gilson et al. |
| 7,670,356 B2 | 3/2010 | Mazzocchi et al. |
| 7,678,123 B2 | 3/2010 | Chanduszko |
| 7,691,121 B2 | 4/2010 | Rosenbluth et al. |
| 7,691,124 B2 | 4/2010 | Balgobin |
| 7,708,770 B2 | 5/2010 | Linder et al. |
| 7,717,929 B2 | 5/2010 | Fallman |
| 7,736,385 B2 | 6/2010 | Agnew |
| 7,749,246 B2 | 7/2010 | McGuckin, Jr. et al. |
| 7,758,606 B2 | 7/2010 | Streeter et al. |
| 7,758,611 B2 | 7/2010 | Kato |
| 7,766,934 B2 | 8/2010 | Pal et al. |
| 7,771,452 B2 | 8/2010 | Pal et al. |
| 7,780,694 B2 | 8/2010 | Palmer et al. |
| 7,780,700 B2 | 8/2010 | Frazier et al. |
| 7,811,305 B2 | 10/2010 | Balgobin et al. |
| 7,815,659 B2 | 10/2010 | Conlon et al. |
| 7,819,893 B2 | 10/2010 | Brady et al. |
| 7,828,815 B2 | 11/2010 | Mazzocchi et al. |
| 7,828,816 B2 | 11/2010 | Mazzocchi et al. |
| 7,833,240 B2 | 11/2010 | Okushi et al. |
| 7,842,053 B2 | 11/2010 | Chanduszko et al. |
| 7,846,175 B2 | 12/2010 | Bonnette et al. |
| 7,846,176 B2 | 12/2010 | Gilson et al. |
| 7,850,708 B2 | 12/2010 | Pal |
| 7,883,516 B2 | 2/2011 | Huang et al. |
| 7,887,560 B2 | 2/2011 | Kusleika |
| 7,901,426 B2 | 3/2011 | Gilson et al. |
| 7,914,549 B2 | 3/2011 | Morsi |
| 7,922,732 B2 | 4/2011 | Mazzocchi et al. |
| 7,927,784 B2 | 4/2011 | Simpson |
| 7,931,659 B2 | 4/2011 | Bose et al. |
| 7,998,165 B2 | 8/2011 | Huffmaster |
| 8,002,822 B2 | 8/2011 | Glocker et al. |
| 8,021,379 B2 | 9/2011 | Thompson et al. |
| 8,021,380 B2 | 9/2011 | Thompson et al. |
| 8,043,326 B2 | 10/2011 | Hancock et al. |
| 8,048,151 B2 | 11/2011 | OBrien et al. |
| 8,052,640 B2 | 11/2011 | Fiorella et al. |
| 8,057,497 B1 | 11/2011 | Raju et al. |
| 8,057,507 B2 | 11/2011 | Horan et al. |
| 8,066,757 B2 | 11/2011 | Ferrera et al. |
| 8,070,791 B2 | 12/2011 | Ferrera et al. |
| 8,088,140 B2 | 1/2012 | Ferrera et al. |
| 8,100,935 B2 | 1/2012 | Rosenbluth et al. |
| 8,109,941 B2 | 2/2012 | Richardson |
| 8,118,829 B2 | 2/2012 | Carrison et al. |
| 8,118,856 B2 | 2/2012 | Schreck et al. |
| 8,123,769 B2 | 2/2012 | Osborne |
| 8,137,376 B2 | 3/2012 | Clubb et al. |
| 8,137,377 B2 | 3/2012 | Palmer et al. |
| 8,142,422 B2 | 3/2012 | Makower et al. |
| 8,142,442 B2 | 3/2012 | Palmer et al. |
| 8,182,508 B2 | 5/2012 | Magnuson et al. |
| 8,187,298 B2 | 5/2012 | Pal |
| 8,246,641 B2 | 8/2012 | Osborne et al. |
| 8,246,672 B2 | 8/2012 | Osborne |
| 8,252,017 B2 | 8/2012 | Paul, Jr. et al. |
| 8,252,018 B2 | 8/2012 | Valaie |
| 8,262,689 B2 | 9/2012 | Schneiderman et al. |
| 8,282,668 B2 | 10/2012 | McGuckin, Jr. et al. |
| 8,287,538 B2 | 10/2012 | Brenzel et al. |
| 8,298,257 B2 | 10/2012 | Sepetka et al. |
| RE43,882 E | 12/2012 | Hopkins et al. |
| 8,357,178 B2 | 1/2013 | Grandfield et al. |
| 8,357,179 B2 | 1/2013 | Grandfield et al. |
| 8,357,180 B2 | 1/2013 | Feller, III et al. |
| 8,357,893 B2 | 1/2013 | Xu et al. |
| 8,361,095 B2 | 1/2013 | Osborne |
| 8,361,110 B2 | 1/2013 | Chanduszko |
| 8,366,663 B2 | 2/2013 | Fiorella et al. |
| 8,409,215 B2 | 4/2013 | Sepetka et al. |
| 8,414,482 B2 | 4/2013 | Belson |
| 8,414,543 B2 | 4/2013 | McGuckin, Jr. et al. |
| 8,419,748 B2 | 4/2013 | Valaie |
| 8,460,312 B2 | 6/2013 | Bose et al. |
| 8,460,313 B2 | 6/2013 | Huffmaster |
| 8,486,104 B2 | 7/2013 | Samson et al. |
| 8,512,352 B2 | 8/2013 | Martin |
| 8,529,596 B2 | 9/2013 | Grandfield et al. |
| 8,545,526 B2 | 10/2013 | Martin et al. |
| 8,574,262 B2 | 11/2013 | Ferrera et al. |
| 8,574,915 B2 | 11/2013 | Zhang et al. |
| 8,579,915 B2 | 11/2013 | French et al. |
| 8,585,713 B2 | 11/2013 | Ferrera et al. |
| 8,608,761 B2 | 12/2013 | Osborne et al. |
| 8,679,142 B2 | 3/2014 | Slee et al. |

(56) References Cited

U.S. PATENT DOCUMENTS

| | | |
|---|---|---|
| 8,690,907 B1 | 4/2014 | Janardhan et al. |
| 8,696,622 B2 | 4/2014 | Fiorella et al. |
| 8,702,652 B2 | 4/2014 | Fiorella et al. |
| 8,702,704 B2 | 4/2014 | Shelton, IV et al. |
| 8,702,724 B2 | 4/2014 | Olsen et al. |
| 8,777,919 B2 | 7/2014 | Kimura et al. |
| 8,777,976 B2 | 7/2014 | Brady et al. |
| 8,777,979 B2 | 7/2014 | Shrivastava et al. |
| 8,784,434 B2 | 7/2014 | Rosenbluth et al. |
| 8,784,441 B2 | 7/2014 | Rosenbluth et al. |
| 8,795,305 B2 | 8/2014 | Martin et al. |
| 8,795,317 B2 | 8/2014 | Grandfield et al. |
| 8,795,345 B2 | 8/2014 | Grandfield et al. |
| 8,814,892 B2 | 8/2014 | Galdonik et al. |
| 8,814,925 B2 | 8/2014 | Hilaire et al. |
| 8,852,205 B2 | 10/2014 | Brady et al. |
| 8,870,941 B2 | 10/2014 | Evans et al. |
| 8,900,265 B1 | 12/2014 | Ulm, III |
| 8,920,358 B2 | 12/2014 | Levine et al. |
| 8,939,991 B2 | 1/2015 | Krolik et al. |
| 8,945,143 B2 | 2/2015 | Ferrera et al. |
| 8,945,160 B2 | 2/2015 | Krolik et al. |
| 8,945,169 B2 | 2/2015 | Pal |
| 8,945,172 B2 | 2/2015 | Ferrera et al. |
| 8,956,399 B2 | 2/2015 | Cam et al. |
| 8,968,330 B2 | 3/2015 | Rosenbluth et al. |
| 9,011,481 B2 | 4/2015 | Aggerholm et al. |
| 9,039,749 B2 | 5/2015 | Shrivastava et al. |
| 9,072,537 B2 | 7/2015 | Grandfield et al. |
| 9,095,342 B2 | 8/2015 | Becking et al. |
| 9,113,936 B2 | 8/2015 | Palmer et al. |
| 9,119,656 B2 | 9/2015 | Bose et al. |
| 9,138,307 B2 | 9/2015 | Valaie |
| 9,155,552 B2 | 10/2015 | Ulm, III |
| 9,161,758 B2 | 10/2015 | Figulla et al. |
| 9,161,766 B2 | 10/2015 | Slee et al. |
| 9,173,668 B2 | 11/2015 | Ulm, III |
| 9,173,688 B2 | 11/2015 | Dosta |
| 9,186,487 B2 | 11/2015 | Dubrul et al. |
| 9,198,687 B2 | 12/2015 | Fulkerson et al. |
| 9,204,887 B2 | 12/2015 | Cully et al. |
| 9,211,132 B2 | 12/2015 | Bowman |
| 9,232,992 B2 | 1/2016 | Heidner et al. |
| 9,254,371 B2 | 2/2016 | Martin et al. |
| 9,301,769 B2 | 4/2016 | Brady et al. |
| 9,332,999 B2 | 5/2016 | Ray et al. |
| 9,402,707 B2 | 8/2016 | Brady et al. |
| 9,445,829 B2 | 9/2016 | Brady et al. |
| 9,456,834 B2 | 10/2016 | Folk |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,104 B2 | 2/2017 | Beckham et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,639 B2 | 5/2017 | Brady et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,898 B2 | 5/2017 | Palepu et al. |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,758,606 B2 | 9/2017 | Lambert et al. |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Peterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,651 B2 | 10/2017 | Harrah et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,304 B2 | 12/2017 | Horan et al. |
| 9,833,604 B2 | 12/2017 | Lam et al. |
| 9,833,625 B2 | 12/2017 | Waldhauser et al. |
| 9,901,434 B2 | 2/2018 | Hoffman |
| 9,918,720 B2 | 3/2018 | Marchand et al. |
| 9,939,361 B2 | 4/2018 | Gaji et al. |
| 10,016,206 B1 | 7/2018 | Yang |
| 10,070,878 B2 | 9/2018 | Ma |
| 10,098,651 B2 | 10/2018 | Marchand et al. |
| 10,201,360 B2 | 2/2019 | Vale et al. |
| 10,231,751 B2 | 3/2019 | Sos |
| 10,292,723 B2 | 5/2019 | Brady et al. |
| 10,299,811 B2 | 5/2019 | Brady et al. |
| 10,363,054 B2 | 7/2019 | Vale et al. |
| 10,376,274 B2 | 8/2019 | Farin et al. |
| 10,390,850 B2 | 8/2019 | Vale et al. |
| 10,524,811 B2 | 1/2020 | Marchand et al. |
| 10,531,942 B2 | 1/2020 | Eggers |
| 10,617,435 B2 | 4/2020 | Vale et al. |
| 10,722,257 B2 | 7/2020 | Skillrud et al. |
| 11,439,418 B2 | 9/2022 | O'Malley |
| 11,517,340 B2 * | 12/2022 | Casey ................. A61B 17/221 |
| 2001/0001315 A1 | 5/2001 | Bates et al. |
| 2001/0016755 A1 | 8/2001 | Addis |
| 2001/0037141 A1 | 11/2001 | Yee et al. |
| 2001/0037171 A1 | 11/2001 | Sato |
| 2001/0041909 A1 | 11/2001 | Tsugita et al. |
| 2001/0044632 A1 | 11/2001 | Daniel et al. |
| 2001/0049554 A1 | 12/2001 | Ruiz et al. |
| 2001/0051810 A1 | 12/2001 | Dubrul et al. |
| 2002/0004667 A1 | 1/2002 | Adams et al. |
| 2002/0016609 A1 | 2/2002 | Wensel et al. |
| 2002/0022859 A1 | 2/2002 | Ogendijk |
| 2002/0026211 A1 | 2/2002 | Khosravi et al. |
| 2002/0042627 A1 | 4/2002 | Brady et al. |
| 2002/0049468 A1 | 4/2002 | Streeter et al. |
| 2002/0052620 A1 | 5/2002 | Barbut |
| 2002/0058911 A1 | 5/2002 | Gilson et al. |
| 2002/0068954 A1 | 6/2002 | Foster |
| 2002/0072764 A1 | 6/2002 | Sepetka et al. |
| 2002/0082558 A1 | 6/2002 | Samson et al. |
| 2002/0091407 A1 * | 7/2002 | Zadno-Azizi ............ B29C 55/04 606/200 |
| 2002/0095171 A1 | 7/2002 | Belef |
| 2002/0123765 A1 | 9/2002 | Sepetka et al. |
| 2002/0128680 A1 | 9/2002 | Pavolvic |
| 2002/0138094 A1 | 9/2002 | Borillo et al. |
| 2002/0143349 A1 | 10/2002 | Gifford, III et al. |
| 2002/0143362 A1 | 10/2002 | Macoviak et al. |

(56) References Cited

U.S. PATENT DOCUMENTS

| | | |
|---|---|---|
| 2002/0156455 A1 | 10/2002 | Barbut |
| 2002/0161393 A1 | 10/2002 | Demond et al. |
| 2002/0165576 A1 | 11/2002 | Boyle et al. |
| 2002/0173819 A1 | 11/2002 | Eeflang et al. |
| 2002/0183787 A1 | 12/2002 | Wahr et al. |
| 2002/0188276 A1 | 12/2002 | Evans et al. |
| 2002/0188314 A1 | 12/2002 | Anderson et al. |
| 2002/0193824 A1 | 12/2002 | Boylan et al. |
| 2002/0198588 A1 | 12/2002 | Armstrong et al. |
| 2003/0004536 A1* | 1/2003 | Boylan ............... A61F 2/0108 606/200 |
| 2003/0004538 A1 | 1/2003 | Secrest et al. |
| 2003/0004540 A1 | 1/2003 | Linder et al. |
| 2003/0004542 A1 | 1/2003 | Wensel et al. |
| 2003/0009146 A1 | 1/2003 | Muni et al. |
| 2003/0009191 A1 | 1/2003 | Wensel et al. |
| 2003/0038447 A1 | 2/2003 | Cantele |
| 2003/0040772 A1 | 2/2003 | Hyodoh et al. |
| 2003/0050663 A1 | 3/2003 | Khachin et al. |
| 2003/0064151 A1 | 4/2003 | Klinedinst |
| 2003/0069520 A1 | 4/2003 | Skujins et al. |
| 2003/0108224 A1 | 6/2003 | Ike |
| 2003/0114879 A1 | 6/2003 | Euteneuer et al. |
| 2003/0125798 A1 | 7/2003 | Martin |
| 2003/0130682 A1 | 7/2003 | Broome et al. |
| 2003/0144687 A1 | 7/2003 | Brady et al. |
| 2003/0144688 A1 | 7/2003 | Brady et al. |
| 2003/0153158 A1 | 8/2003 | Ho et al. |
| 2003/0153943 A1 | 8/2003 | Michael et al. |
| 2003/0153944 A1 | 8/2003 | Phung et al. |
| 2003/0163064 A1 | 8/2003 | Vrba et al. |
| 2003/0163158 A1 | 8/2003 | White |
| 2003/0171769 A1 | 9/2003 | Barbut |
| 2003/0171771 A1 | 9/2003 | Anderson et al. |
| 2003/0176884 A1 | 9/2003 | Berrada et al. |
| 2003/0187495 A1 | 10/2003 | Cully et al. |
| 2003/0195537 A1 | 10/2003 | Dubrul et al. |
| 2003/0195554 A1 | 10/2003 | Shen et al. |
| 2003/0199917 A1 | 10/2003 | Knudson et al. |
| 2003/0204202 A1 | 10/2003 | Palmer et al. |
| 2003/0208224 A1 | 11/2003 | Broome |
| 2003/0212430 A1 | 11/2003 | Bose et al. |
| 2003/0236533 A1 | 12/2003 | Wilson et al. |
| 2004/0064179 A1 | 4/2004 | Linder et al. |
| 2004/0068288 A1 | 4/2004 | Palmer et al. |
| 2004/0073243 A1 | 4/2004 | Sepetka et al. |
| 2004/0079429 A1 | 4/2004 | Miller et al. |
| 2004/0082962 A1 | 4/2004 | Demarais et al. |
| 2004/0082967 A1* | 4/2004 | Broome ............... A61F 2/011 606/200 |
| 2004/0088001 A1 | 5/2004 | Bosma et al. |
| 2004/0093065 A1 | 5/2004 | Yachia et al. |
| 2004/0098050 A1 | 5/2004 | Foerster et al. |
| 2004/0133231 A1 | 7/2004 | Maitland et al. |
| 2004/0133232 A1 | 7/2004 | Rosenbluth et al. |
| 2004/0138692 A1 | 7/2004 | Phung et al. |
| 2004/0153117 A1 | 8/2004 | Clubb et al. |
| 2004/0153118 A1 | 8/2004 | Clubb et al. |
| 2004/0199201 A1 | 10/2004 | Kellett et al. |
| 2004/0204749 A1 | 10/2004 | Gunderson |
| 2004/0215318 A1 | 10/2004 | Kwitkin |
| 2004/0220663 A1 | 11/2004 | Rivelli |
| 2005/0010245 A1 | 1/2005 | Wasicek |
| 2005/0033248 A1 | 2/2005 | Machida et al. |
| 2005/0033348 A1 | 2/2005 | Sepetka et al. |
| 2005/0038447 A1 | 2/2005 | Huffmaster |
| 2005/0038468 A1 | 2/2005 | Panetta et al. |
| 2005/0043759 A1 | 2/2005 | Chanduszko |
| 2005/0049619 A1 | 3/2005 | Sepetka et al. |
| 2005/0049669 A1 | 3/2005 | Jones et al. |
| 2005/0049670 A1 | 3/2005 | Jones et al. |
| 2005/0055033 A1 | 3/2005 | Leslie et al. |
| 2005/0055047 A1 | 3/2005 | Greenhalgh |
| 2005/0058837 A1 | 3/2005 | Farnworth et al. |
| 2005/0059995 A1 | 3/2005 | Sepetka et al. |
| 2005/0085849 A1 | 4/2005 | Sepetka et al. |
| 2005/0090779 A1 | 4/2005 | Osypka |
| 2005/0090857 A1 | 4/2005 | Kusleika et al. |
| 2005/0125024 A1 | 6/2005 | Sepetka et al. |
| 2005/0149997 A1 | 7/2005 | Wolozin et al. |
| 2005/0171566 A1 | 8/2005 | Kanamaru |
| 2005/0173135 A1 | 8/2005 | Almen |
| 2005/0192627 A1 | 9/2005 | Whisenant et al. |
| 2005/0215942 A1 | 9/2005 | Abrahamson et al. |
| 2005/0216030 A1 | 9/2005 | Sepetka et al. |
| 2005/0216050 A1 | 9/2005 | Sepetka et al. |
| 2005/0228417 A1 | 10/2005 | Teitelbaum et al. |
| 2005/0251206 A1 | 11/2005 | Maahs et al. |
| 2005/0251209 A1 | 11/2005 | Saadat et al. |
| 2005/0267491 A1 | 12/2005 | Kellett et al. |
| 2005/0273135 A1 | 12/2005 | Chanduszko et al. |
| 2005/0283186 A1 | 12/2005 | Berrada et al. |
| 2005/0288686 A1 | 12/2005 | Sepetka et al. |
| 2006/0008332 A1 | 1/2006 | Greenberg et al. |
| 2006/0009798 A1 | 1/2006 | Callister et al. |
| 2006/0009799 A1 | 1/2006 | Kleshinski et al. |
| 2006/0020285 A1 | 1/2006 | Niermann |
| 2006/0020286 A1 | 1/2006 | Niermann |
| 2006/0030877 A1 | 2/2006 | Martinez et al. |
| 2006/0041228 A1 | 2/2006 | Vo et al. |
| 2006/0058836 A1 | 3/2006 | Bose et al. |
| 2006/0058837 A1 | 3/2006 | Bose et al. |
| 2006/0058838 A1 | 3/2006 | Bose et al. |
| 2006/0064151 A1 | 3/2006 | Guterman et al. |
| 2006/0069424 A1 | 3/2006 | Acosta et al. |
| 2006/0074477 A1 | 4/2006 | Berthiaume et al. |
| 2006/0142838 A1 | 6/2006 | Molaei et al. |
| 2006/0149313 A1 | 7/2006 | Arguello et al. |
| 2006/0155305 A1 | 7/2006 | Freudenthal et al. |
| 2006/0161187 A1 | 7/2006 | Evine et al. |
| 2006/0195137 A1 | 8/2006 | Sepetka et al. |
| 2006/0224177 A1 | 10/2006 | Finitsis |
| 2006/0224179 A1 | 10/2006 | Kucharczyk et al. |
| 2006/0229638 A1 | 10/2006 | Abrams et al. |
| 2006/0235501 A1 | 10/2006 | Igaki |
| 2006/0241677 A1 | 10/2006 | Johnson et al. |
| 2006/0282111 A1 | 12/2006 | Morsi |
| 2006/0287668 A1 | 12/2006 | Fawzi et al. |
| 2006/0287701 A1 | 12/2006 | Pal |
| 2006/0293706 A1 | 12/2006 | Shimon |
| 2007/0010857 A1 | 1/2007 | Sugimoto et al. |
| 2007/0032879 A1 | 2/2007 | Levine et al. |
| 2007/0088382 A1 | 4/2007 | Bei et al. |
| 2007/0088383 A1* | 4/2007 | Pal ............... A61F 2/012 606/200 |
| 2007/0100348 A1 | 5/2007 | Cauthen, III et al. |
| 2007/0118173 A1 | 5/2007 | Magnuson et al. |
| 2007/0149972 A1 | 6/2007 | Muller |
| 2007/0156170 A1 | 7/2007 | Hancock et al. |
| 2007/0165170 A1 | 7/2007 | Fukuda |
| 2007/0179527 A1 | 8/2007 | Eskuri et al. |
| 2007/0191866 A1 | 8/2007 | Palmer et al. |
| 2007/0198028 A1 | 8/2007 | Miloslavski et al. |
| 2007/0198051 A1 | 8/2007 | Clubb et al. |
| 2007/0198075 A1 | 8/2007 | Levy |
| 2007/0208367 A1 | 9/2007 | Fiorella et al. |
| 2007/0208371 A1 | 9/2007 | French et al. |
| 2007/0225749 A1 | 9/2007 | Martin et al. |
| 2007/0233175 A1 | 10/2007 | Zaver et al. |
| 2007/0244505 A1 | 10/2007 | Gilson et al. |
| 2007/0270902 A1 | 11/2007 | Slazas et al. |
| 2007/0288054 A1 | 12/2007 | Tanaka et al. |
| 2008/0045881 A1 | 2/2008 | Teitelbaum et al. |
| 2008/0077227 A1 | 3/2008 | Ouellette et al. |
| 2008/0082107 A1 | 4/2008 | Miller et al. |
| 2008/0086190 A1 | 4/2008 | Ta |
| 2008/0091223 A1 | 4/2008 | Pokorney et al. |
| 2008/0097386 A1 | 4/2008 | Osypka |
| 2008/0109031 A1 | 5/2008 | Sepetka et al. |
| 2008/0109032 A1 | 5/2008 | Sepetka et al. |
| 2008/0119886 A1 | 5/2008 | Greenhalgh et al. |
| 2008/0125798 A1 | 5/2008 | Osborne et al. |
| 2008/0177296 A1 | 7/2008 | Sepetka et al. |
| 2008/0178890 A1 | 7/2008 | Townsend et al. |

(56) References Cited

U.S. PATENT DOCUMENTS

| | | |
|---|---|---|
| 2008/0183197 A1 | 7/2008 | Sepetka et al. |
| 2008/0183198 A1 | 7/2008 | Sepetka et al. |
| 2008/0183205 A1 | 7/2008 | Sepetka et al. |
| 2008/0188876 A1 | 8/2008 | Sepetka et al. |
| 2008/0188885 A1 | 8/2008 | Sepetka et al. |
| 2008/0188887 A1 | 8/2008 | Batiste |
| 2008/0200946 A1 | 8/2008 | Braun et al. |
| 2008/0200947 A1 | 8/2008 | Kusleika et al. |
| 2008/0215077 A1 | 9/2008 | Sepetka et al. |
| 2008/0221600 A1 | 9/2008 | Dieck et al. |
| 2008/0228209 A1 | 9/2008 | DeMello et al. |
| 2008/0234706 A1 | 9/2008 | Sepetka et al. |
| 2008/0243170 A1 | 10/2008 | Jenson et al. |
| 2008/0255596 A1 | 10/2008 | Jenson et al. |
| 2008/0262410 A1 | 10/2008 | Jenson et al. |
| 2008/0262528 A1 | 10/2008 | Martin |
| 2008/0262532 A1 | 10/2008 | Martin |
| 2008/0262590 A1 | 10/2008 | Murray |
| 2008/0269871 A1 | 10/2008 | Eli |
| 2008/0275488 A1 | 11/2008 | Fleming |
| 2008/0275493 A1 | 11/2008 | Farmiga |
| 2008/0281350 A1 | 11/2008 | Sepetka et al. |
| 2008/0312681 A1 | 12/2008 | Ansel et al. |
| 2009/0005858 A1 | 1/2009 | Young et al. |
| 2009/0024157 A1 | 1/2009 | Anukhin |
| 2009/0030443 A1 | 1/2009 | Buser et al. |
| 2009/0062841 A1 | 3/2009 | Amplatz et al. |
| 2009/0069828 A1 | 3/2009 | Martin et al. |
| 2009/0076539 A1 | 3/2009 | Valaie |
| 2009/0088793 A1 | 4/2009 | Bagaoisan et al. |
| 2009/0088795 A1 | 4/2009 | Cahill |
| 2009/0105722 A1 | 4/2009 | Fulkerson et al. |
| 2009/0105737 A1 | 4/2009 | Fulkerson et al. |
| 2009/0105747 A1 | 4/2009 | Chanduszko et al. |
| 2009/0149881 A1 | 6/2009 | Vale et al. |
| 2009/0163851 A1 | 6/2009 | Holloway et al. |
| 2009/0177206 A1 | 7/2009 | Lozier et al. |
| 2009/0182336 A1 | 7/2009 | Brenzel et al. |
| 2009/0281610 A1 | 11/2009 | Parker |
| 2009/0281619 A1 | 11/2009 | Le et al. |
| 2009/0287229 A1 | 11/2009 | Ogdahl |
| 2009/0292297 A1 | 11/2009 | Ferrere |
| 2009/0292307 A1 | 11/2009 | Razack |
| 2009/0299393 A1 | 12/2009 | Martin et al. |
| 2009/0299403 A1 | 12/2009 | Chanduszko et al. |
| 2009/0306702 A1 | 12/2009 | Miloslavski et al. |
| 2009/0326636 A1 | 12/2009 | Hashimoto et al. |
| 2010/0004607 A1 | 1/2010 | Wilson et al. |
| 2010/0076482 A1 | 3/2010 | Shu et al. |
| 2010/0087850 A1 | 4/2010 | Razack |
| 2010/0087908 A1 | 4/2010 | Hilaire et al. |
| 2010/0114017 A1 | 5/2010 | Lenker et al. |
| 2010/0125326 A1 | 5/2010 | Kalstad et al. |
| 2010/0125327 A1 | 5/2010 | Agnew |
| 2010/0191272 A1 | 7/2010 | Keating |
| 2010/0211094 A1 | 8/2010 | Sargent, Jr. |
| 2010/0268264 A1 | 10/2010 | Bonnette et al. |
| 2010/0268265 A1 | 10/2010 | Krolik et al. |
| 2010/0274277 A1 | 10/2010 | Eaton |
| 2010/0318178 A1 | 12/2010 | Rapaport et al. |
| 2010/0324649 A1 | 12/2010 | Mattsson et al. |
| 2010/0331949 A1 | 12/2010 | Habib |
| 2011/0009875 A1 | 1/2011 | Grandfield et al. |
| 2011/0009940 A1 | 1/2011 | Grandfield et al. |
| 2011/0009950 A1 | 1/2011 | Grandfield et al. |
| 2011/0015718 A1 | 1/2011 | Schreck |
| 2011/0022149 A1 | 1/2011 | Cox et al. |
| 2011/0040319 A1 | 2/2011 | Fulton, III |
| 2011/0054287 A1 | 3/2011 | Schultz |
| 2011/0054504 A1 | 3/2011 | Porter |
| 2011/0054514 A1 | 3/2011 | Arcand et al. |
| 2011/0054516 A1 | 3/2011 | Keegan et al. |
| 2011/0060212 A1 | 3/2011 | Slee et al. |
| 2011/0060359 A1 | 3/2011 | Hannes et al. |
| 2011/0106137 A1 | 5/2011 | Shimon |
| 2011/0125181 A1 | 5/2011 | Brady et al. |
| 2011/0152920 A1 | 6/2011 | Eckhouse et al. |
| 2011/0160763 A1 | 6/2011 | Ferrera et al. |
| 2011/0166586 A1 | 7/2011 | Sepetka et al. |
| 2011/0184456 A1 | 7/2011 | Grandfield et al. |
| 2011/0196414 A1 | 8/2011 | Porter et al. |
| 2011/0202088 A1 | 8/2011 | Eckhouse et al. |
| 2011/0208233 A1 | 8/2011 | McGuckin, Jr. et al. |
| 2011/0213297 A1 | 9/2011 | Aklog et al. |
| 2011/0213393 A1 | 9/2011 | Aklog et al. |
| 2011/0213403 A1 | 9/2011 | Aboytes |
| 2011/0224707 A1 | 9/2011 | Miloslavski et al. |
| 2011/0270374 A1 | 11/2011 | Orr et al. |
| 2011/0276120 A1 | 11/2011 | Gilson et al. |
| 2011/0319917 A1 | 12/2011 | Ferrera et al. |
| 2012/0041449 A1 | 2/2012 | Eckhouse et al. |
| 2012/0041474 A1 | 2/2012 | Eckhouse et al. |
| 2012/0059356 A1 | 3/2012 | di Palma et al. |
| 2012/0065660 A1 | 3/2012 | Ferrera et al. |
| 2012/0083823 A1 | 4/2012 | Shrivastava et al. |
| 2012/0083868 A1 | 4/2012 | Shrivastava et al. |
| 2012/0089216 A1 | 4/2012 | Rapaport et al. |
| 2012/0101510 A1 | 4/2012 | Lenker et al. |
| 2012/0116440 A1 | 5/2012 | Leynov et al. |
| 2012/0123466 A1 | 5/2012 | Porter et al. |
| 2012/0022572 A1 | 6/2012 | Braun et al. |
| 2012/0143230 A1 | 6/2012 | Sepetka et al. |
| 2012/0143237 A1 | 6/2012 | Cam et al. |
| 2012/0143317 A1 | 6/2012 | Cam et al. |
| 2012/0150147 A1 | 6/2012 | Leynov et al. |
| 2012/0165858 A1 | 6/2012 | Eckhouse et al. |
| 2012/0165859 A1 | 6/2012 | Eckhouse et al. |
| 2012/0209312 A1 | 8/2012 | Aggerholm et al. |
| 2012/0215250 A1 | 8/2012 | Grandfield et al. |
| 2012/0277788 A1 | 11/2012 | Cattaneo |
| 2012/0283768 A1 | 11/2012 | Cox et al. |
| 2012/0296362 A1 | 11/2012 | Cam et al. |
| 2012/0316600 A1 | 12/2012 | Ferrera et al. |
| 2012/0330350 A1 | 12/2012 | Jones et al. |
| 2013/0030460 A1 | 1/2013 | Marks et al. |
| 2013/0030461 A1 | 1/2013 | Marks et al. |
| 2013/0046330 A1* | 2/2013 | McIntosh ................ A61F 2/012 |
| | | 606/200 |
| 2013/0046333 A1 | 2/2013 | Jones et al. |
| 2013/0046334 A1 | 2/2013 | Jones et al. |
| 2013/0116774 A1 | 5/2013 | Strauss et al. |
| 2013/0131614 A1 | 5/2013 | Hassan et al. |
| 2013/0144311 A1 | 6/2013 | Fung et al. |
| 2013/0144326 A1 | 6/2013 | Brady et al. |
| 2013/0158591 A1 | 6/2013 | Koehler |
| 2013/0158592 A1 | 6/2013 | Porter |
| 2013/0184739 A1 | 7/2013 | Brady et al. |
| 2013/0197567 A1 | 8/2013 | Brady et al. |
| 2013/0226146 A1 | 8/2013 | Tekulve |
| 2013/0268050 A1 | 10/2013 | Wilson et al. |
| 2013/0271788 A1 | 10/2013 | Utsunomiya |
| 2013/0277079 A1 | 10/2013 | Tsuzuki et al. |
| 2013/0281788 A1 | 10/2013 | Garrison |
| 2013/0325051 A1 | 12/2013 | Martin et al. |
| 2013/0325055 A1 | 12/2013 | Eckhouse et al. |
| 2013/0325056 A1 | 12/2013 | Eckhouse et al. |
| 2013/0345739 A1 | 12/2013 | Brady et al. |
| 2014/0005712 A1 | 1/2014 | Martin |
| 2014/0005713 A1 | 1/2014 | Bowman |
| 2014/0046359 A1 | 2/2014 | Bowman et al. |
| 2014/0088678 A1 | 3/2014 | Wainwright et al. |
| 2014/0121672 A1 | 5/2014 | Folk |
| 2014/0128905 A1 | 5/2014 | Molaei |
| 2014/0134654 A1 | 5/2014 | Rudel et al. |
| 2014/0135812 A1 | 5/2014 | Divino et al. |
| 2014/0142598 A1 | 5/2014 | Fulton, III |
| 2014/0163367 A1 | 6/2014 | Eskuri |
| 2014/0180122 A1 | 6/2014 | Stigall et al. |
| 2014/0180377 A1 | 6/2014 | Bose et al. |
| 2014/0180397 A1 | 6/2014 | Gerberding et al. |
| 2014/0183077 A1 | 7/2014 | Rosendall et al. |
| 2014/0194911 A1 | 7/2014 | Johnson et al. |
| 2014/0194919 A1 | 7/2014 | Losordo et al. |
| 2014/0200607 A1 | 7/2014 | Sepetka et al. |

(56) References Cited

U.S. PATENT DOCUMENTS

| | | |
|---|---|---|
| 2014/0200608 A1 | 7/2014 | Brady et al. |
| 2014/0236220 A1 | 8/2014 | Inoue |
| 2014/0243881 A1 | 8/2014 | Lees et al. |
| 2014/0257362 A1 | 9/2014 | Eidenschink |
| 2014/0276922 A1 | 9/2014 | McLain et al. |
| 2014/0277079 A1 | 9/2014 | Vale et al. |
| 2014/0303667 A1 | 10/2014 | Cox et al. |
| 2014/0309657 A1 | 10/2014 | Ben-Ami |
| 2014/0309673 A1 | 10/2014 | Dacuycuy et al. |
| 2014/0330302 A1 | 11/2014 | Tekulve et al. |
| 2014/0343585 A1 | 11/2014 | Ferrera et al. |
| 2014/0371769 A1 | 12/2014 | Vale et al. |
| 2014/0371779 A1 | 12/2014 | Vale et al. |
| 2014/0371780 A1 | 12/2014 | Vale et al. |
| 2014/0372779 A1 | 12/2014 | Wong et al. |
| 2014/0379023 A1 | 12/2014 | Brady et al. |
| 2015/0018859 A1 | 1/2015 | Quick et al. |
| 2015/0018860 A1 | 1/2015 | Quick et al. |
| 2015/0032144 A1 | 1/2015 | Holloway |
| 2015/0080937 A1 | 3/2015 | Davidson |
| 2015/0112376 A1 | 4/2015 | Molaei et al. |
| 2015/0133990 A1 | 5/2015 | Davidson |
| 2015/0150672 A1 | 6/2015 | Ma |
| 2015/0164523 A1 | 6/2015 | Brady et al. |
| 2015/0224133 A1 | 8/2015 | Ohri et al. |
| 2015/0250497 A1 | 9/2015 | Marks et al. |
| 2015/0257775 A1 | 9/2015 | Gilvarry et al. |
| 2015/0272716 A1 | 10/2015 | Pinchuk et al. |
| 2015/0297252 A1 | 10/2015 | Miloslavski et al. |
| 2015/0313617 A1 | 11/2015 | Grandfield et al. |
| 2015/0320431 A1 | 11/2015 | John |
| 2015/0352325 A1 | 12/2015 | Quick |
| 2015/0359547 A1 | 12/2015 | Vale et al. |
| 2015/0366650 A1 | 12/2015 | Zi et al. |
| 2015/0374391 A1 | 12/2015 | Quick et al. |
| 2015/0374393 A1 | 12/2015 | Brady et al. |
| 2015/0374479 A1 | 12/2015 | Vale |
| 2016/0015402 A1 | 1/2016 | Brady et al. |
| 2016/0022269 A1 | 1/2016 | Ganske et al. |
| 2016/0022296 A1 | 1/2016 | Brady et al. |
| 2016/0045298 A1 | 2/2016 | Thinnes, Jr. et al. |
| 2016/0066921 A1 | 3/2016 | Seifert et al. |
| 2016/0100928 A1 | 4/2016 | Lees et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113664 A1 | 4/2016 | Brady et al. |
| 2016/0113665 A1 | 4/2016 | Brady et al. |
| 2016/0120558 A1 | 5/2016 | Brady et al. |
| 2016/0143653 A1 | 5/2016 | Vale et al. |
| 2016/0192953 A1 | 7/2016 | Brady et al. |
| 2016/0192954 A1 | 7/2016 | Brady et al. |
| 2016/0192955 A1 | 7/2016 | Brady et al. |
| 2016/0192956 A1 | 7/2016 | Brady et al. |
| 2016/0256180 A1 | 9/2016 | Vale et al. |
| 2016/0303381 A1 | 10/2016 | Pierce et al. |
| 2016/0317168 A1 | 11/2016 | Brady et al. |
| 2017/0007264 A1 | 1/2017 | Cruise et al. |
| 2017/0007265 A1 | 1/2017 | Guo et al. |
| 2017/0020542 A1 | 1/2017 | Martin et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0056061 A1 | 3/2017 | Ogle et al. |
| 2017/0071614 A1 | 3/2017 | Vale et al. |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Am et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086862 A1 | 3/2017 | Vale et al. |
| 2017/0086863 A1 | 3/2017 | Brady et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Grandfield |
| 2017/0100183 A1 | 4/2017 | Aizzo et al. |
| 2017/0105743 A1 | 4/2017 | Vale et al. |
| 2017/0112515 A1 | 4/2017 | Brady et al. |
| 2017/0112647 A1 | 4/2017 | Sachar et al. |
| 2017/0113023 A1 | 4/2017 | Steingisser et al. |
| 2017/0119409 A1 | 5/2017 | Ma |
| 2017/0143465 A1 | 5/2017 | Ulm, III |
| 2017/0147765 A1 | 5/2017 | Mehta |
| 2017/0150979 A1 | 6/2017 | John |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0189041 A1 | 7/2017 | Cox et al. |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1* | 10/2017 | Greenhalgh ..... A61B 17/22012 |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2018/0140315 A1 | 5/2018 | Bowman et al. |
| 2018/0206865 A1 | 7/2018 | Martin et al. |
| 2018/0207399 A1 | 7/2018 | Chou et al. |
| 2018/0263650 A1 | 9/2018 | Wanami et al. |
| 2018/0325537 A1 | 11/2018 | Shamay et al. |
| 2018/0326024 A1 | 11/2018 | Prochazka et al. |
| 2018/0344338 A1 | 12/2018 | Brady et al. |
| 2019/0000492 A1 | 1/2019 | Casey et al. |
| 2019/0015061 A1 | 1/2019 | Liebeskind et al. |
| 2019/0167284 A1 | 6/2019 | Friedman et al. |

(56) References Cited

U.S. PATENT DOCUMENTS

| | | |
|---|---|---|
| 2019/0239907 A1* | 8/2019 | Brady .............. A61B 17/22031 |
| 2019/0292273 A1 | 9/2019 | Hanotin et al. |
| 2019/0374239 A1 | 12/2019 | Martin et al. |
| 2019/0380723 A1 | 12/2019 | Grandfield et al. |
| 2019/0388097 A1 | 12/2019 | Girdhar et al. |
| 2020/0000483 A1 | 1/2020 | Brady et al. |
| 2020/0009150 A1 | 1/2020 | Chamorro Sanchez |
| 2020/0085444 A1 | 3/2020 | Vale et al. |
| 2020/0100804 A1 | 4/2020 | Casey et al. |
| 2020/0297364 A1 | 9/2020 | Choe et al. |
| 2020/0390459 A1* | 12/2020 | Casey .................... A61F 2/915 |
| 2021/0005321 A1 | 1/2021 | Hwang |
| 2021/0007757 A1 | 1/2021 | Casey et al. |
| 2021/0228223 A1 | 7/2021 | Casey et al. |
| 2022/0192739 A1 | 6/2022 | Deen et al. |

FOREIGN PATENT DOCUMENTS

| | | |
|---|---|---|
| CN | 102307613 A | 1/2012 |
| CN | 102316809 A | 1/2012 |
| CN | 102596098 A | 7/2012 |
| CN | 103764049 A | 4/2014 |
| CN | 104042304 A | 9/2014 |
| CN | 105208950 A | 12/2015 |
| CN | 105662532 A | 6/2016 |
| CN | 205359559 U | 7/2016 |
| CN | 107530090 A | 1/2018 |
| CN | 208582467 U | 3/2019 |
| DE | 202009001951 U1 | 3/2010 |
| DE | 102009056450 A1 | 6/2011 |
| DE | 102010010849 A1 | 9/2011 |
| DE | 102010014778 A1 | 10/2011 |
| DE | 102010024085 A1 | 12/2011 |
| DE | 102011014586 B3 | 9/2012 |
| EP | 1153581 A1 | 11/2001 |
| EP | 2301450 A1 | 3/2011 |
| EP | 2438891 A1 | 4/2012 |
| EP | 2628455 A1 | 8/2013 |
| EP | 3156004 A1 | 4/2017 |
| EP | 3593742 A1 | 1/2020 |
| EP | 3669802 A1 | 6/2020 |
| EP | 3858291 A1 | 8/2021 |
| ES | 2210456 T3 | 7/2004 |
| GB | 2427554 A | 1/2007 |
| GB | 2494820 A | 3/2013 |
| JP | H0919438 A | 1/1997 |
| JP | 2014511223 A | 5/2014 |
| JP | 2014525796 A | 10/2014 |
| JP | 2015-505250 A | 2/2015 |
| JP | 2016-513505 A | 5/2016 |
| JP | 2019-526365 A | 9/2019 |
| WO | 9424926 A1 | 11/1994 |
| WO | 9727808 A1 | 8/1997 |
| WO | 9738631 A1 | 10/1997 |
| WO | 9920335 A1 | 4/1999 |
| WO | 9956801 A2 | 11/1999 |
| WO | 9960933 A1 | 12/1999 |
| WO | 0121077 A1 | 3/2001 |
| WO | 0202162 A2 | 1/2002 |
| WO | 0211627 A2 | 2/2002 |
| WO | 0243616 A2 | 6/2002 |
| WO | 02070061 A1 | 9/2002 |
| WO | 02094111 A2 | 11/2002 |
| WO | 03002006 A1 | 1/2003 |
| WO | 03030751 A1 | 4/2003 |
| WO | 03051448 A2 | 6/2003 |
| WO | 2004028571 A2 | 4/2004 |
| WO | 2004056275 A1 | 7/2004 |
| WO | 2005000130 A1 | 1/2005 |
| WO | 2005027779 A2 | 3/2005 |
| WO | 2006021407 A2 | 3/2006 |
| WO | 2006031410 A2 | 3/2006 |
| WO | 2006107641 A2 | 10/2006 |
| WO | 2006135823 A2 | 12/2006 |
| WO | 2007054307 A2 | 5/2007 |
| WO | 2007068424 A2 | 6/2007 |
| WO | 2008034615 A2 | 3/2008 |
| WO | 2008051431 A1 | 5/2008 |
| WO | 2008131116 A1 | 10/2008 |
| WO | 2008135823 A1 | 11/2008 |
| WO | 2009031338 A1 | 3/2009 |
| WO | 2009076482 A1 | 6/2009 |
| WO | 2009086482 A1 | 7/2009 |
| WO | 2009105710 A1 | 8/2009 |
| WO | 2010010545 A1 | 1/2010 |
| WO | 2010046897 A1 | 4/2010 |
| WO | 2010075565 A2 | 7/2010 |
| WO | 2010102307 A1 | 9/2010 |
| WO | 2010146581 A1 | 12/2010 |
| WO | 2011013556 A1 | 2/2011 |
| WO | 2011066961 A1 | 6/2011 |
| WO | 2011082319 A1 | 7/2011 |
| WO | 2011095352 A1 | 8/2011 |
| WO | 2011106426 A1 | 9/2011 |
| WO | 2011110316 A1 | 9/2011 |
| WO | 2011135556 A1 | 11/2011 |
| WO | 2012052982 A1 | 4/2012 |
| WO | 2012064726 A1 | 5/2012 |
| WO | 2012081020 A1 | 6/2012 |
| WO | 2012110619 A1 | 8/2012 |
| WO | 2012120490 A2 | 9/2012 |
| WO | 2012156924 A1 | 11/2012 |
| WO | 2013016435 A1 | 1/2013 |
| WO | 2013072777 A2 | 5/2013 |
| WO | 2013105099 A2 | 7/2013 |
| WO | 2013109756 A2 | 7/2013 |
| WO | 2013187927 A1 | 12/2013 |
| WO | 2014047650 A1 | 3/2014 |
| WO | 2014081892 A1 | 5/2014 |
| WO | 2014139845 A1 | 9/2014 |
| WO | 2014169266 A1 | 10/2014 |
| WO | 2014178198 A1 | 11/2014 |
| WO | 2015061365 A1 | 4/2015 |
| WO | 2015103547 A1 | 7/2015 |
| WO | 2015134625 A1 | 9/2015 |
| WO | 2015179324 A2 | 11/2015 |
| WO | 2015189354 A1 | 12/2015 |
| WO | 2016010995 A1 | 1/2016 |
| WO | 2016089451 A1 | 6/2016 |
| WO | 2017089424 A1 | 6/2017 |
| WO | WO 2017/090473 A1 | 6/2017 |
| WO | WO 2017/103686 A2 | 6/2017 |
| WO | WO 2017/161204 A1 | 9/2017 |
| WO | WO 2020/039082 A1 | 2/2020 |
| WO | WO 2021/113302 A1 | 6/2021 |

* cited by examiner

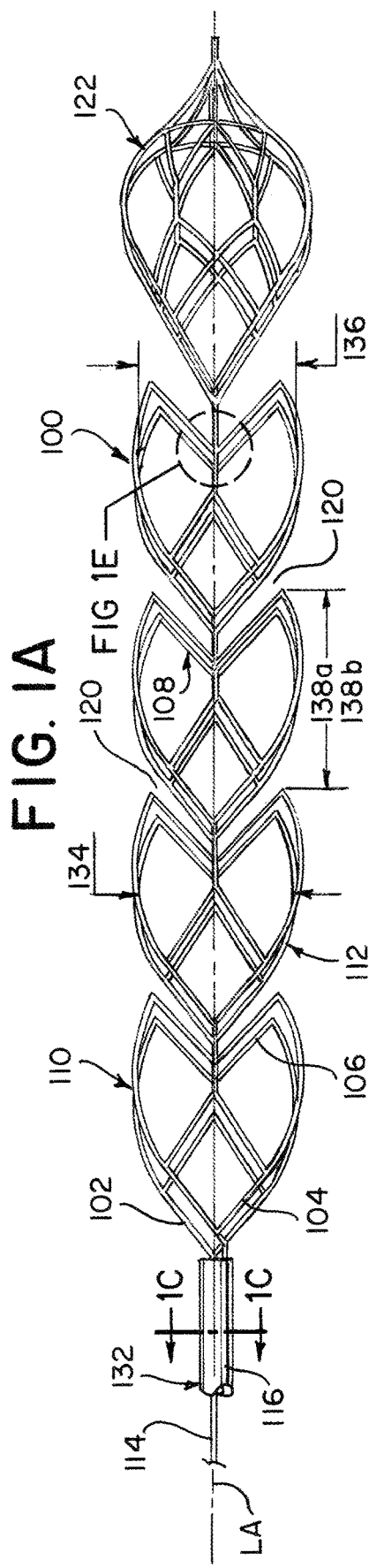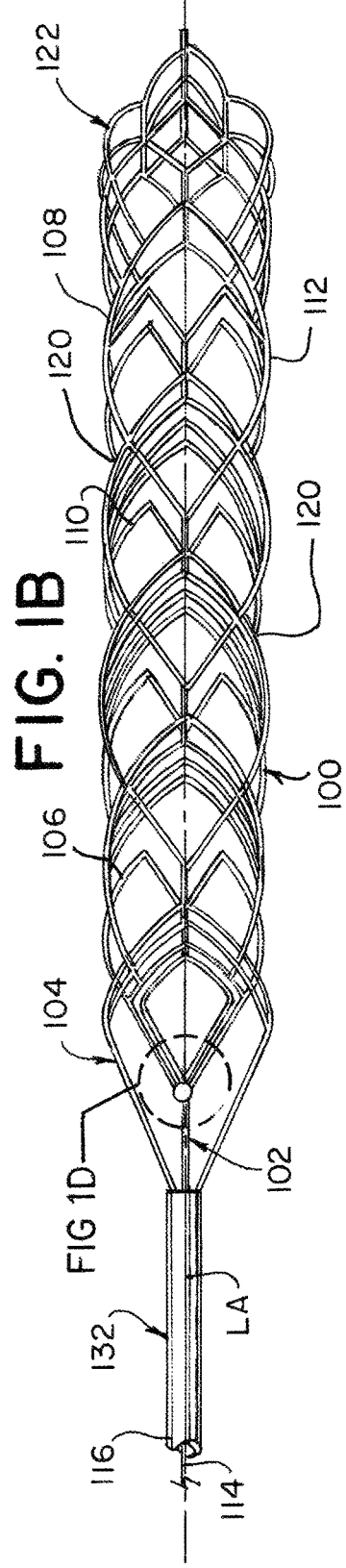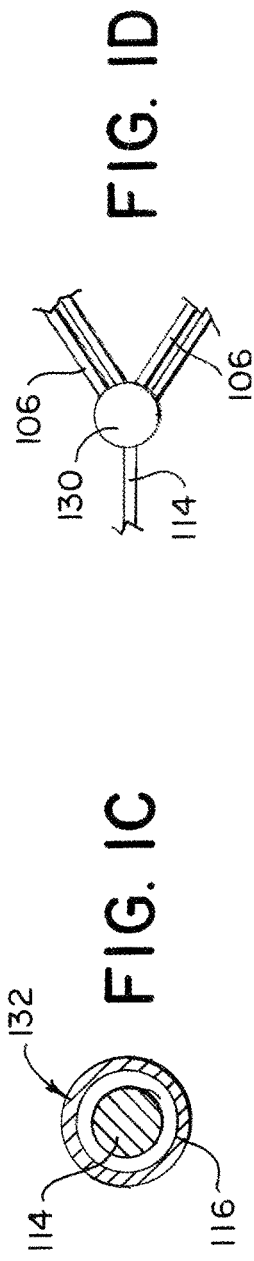

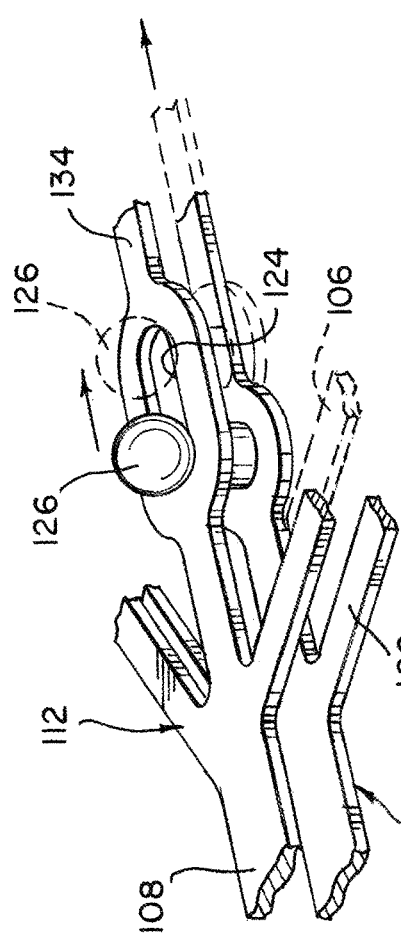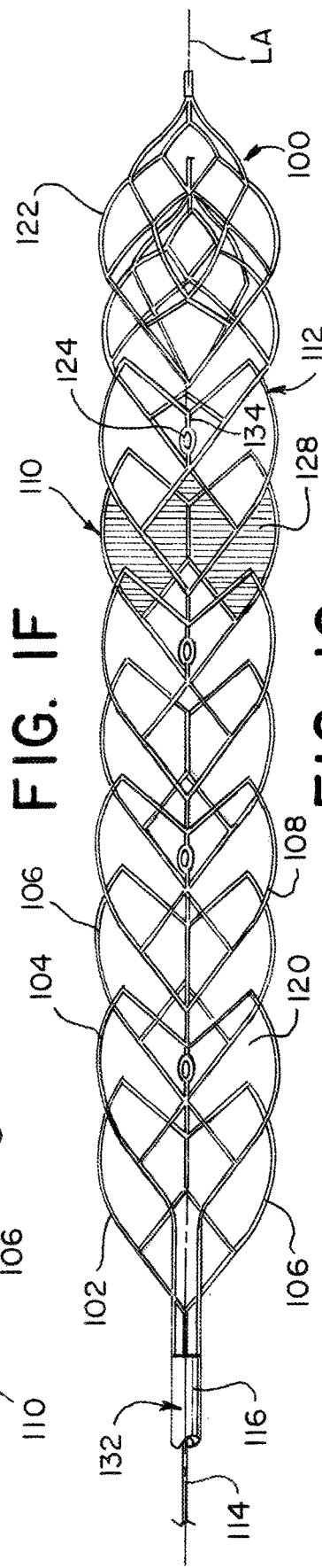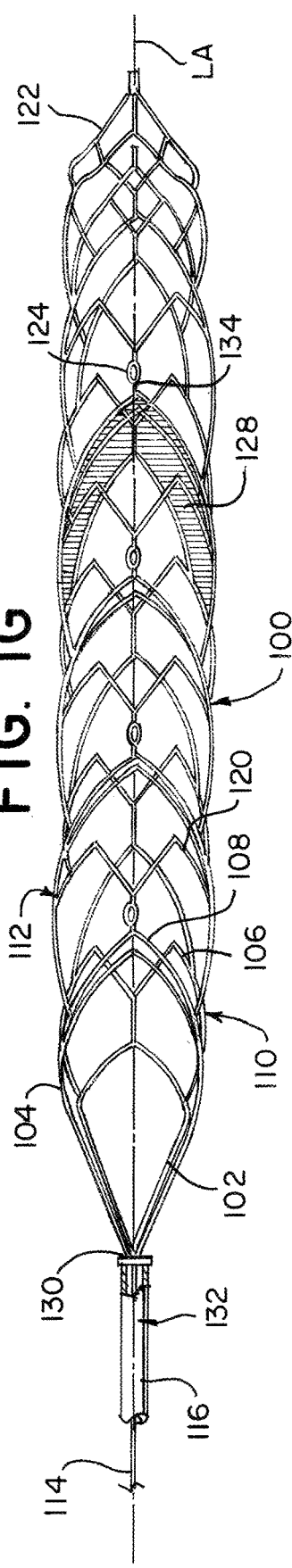

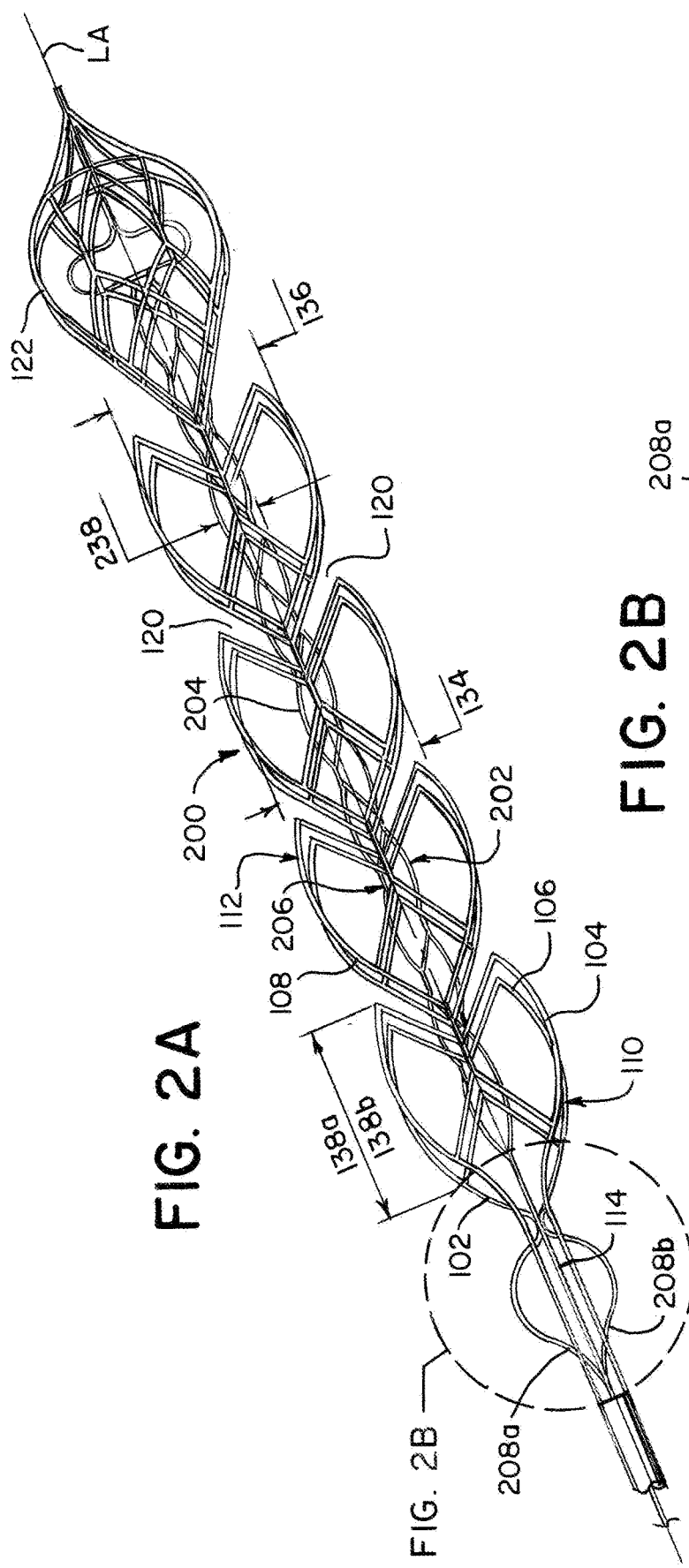
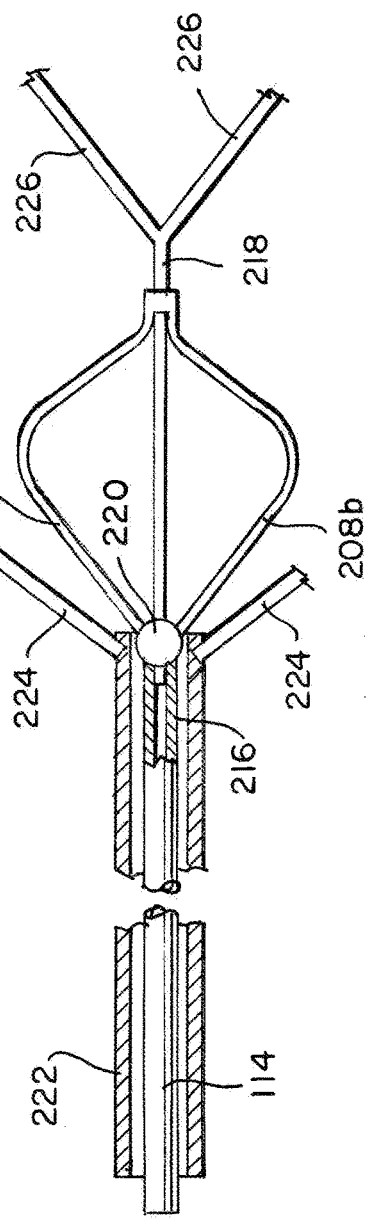
FIG. 2A
FIG. 2B

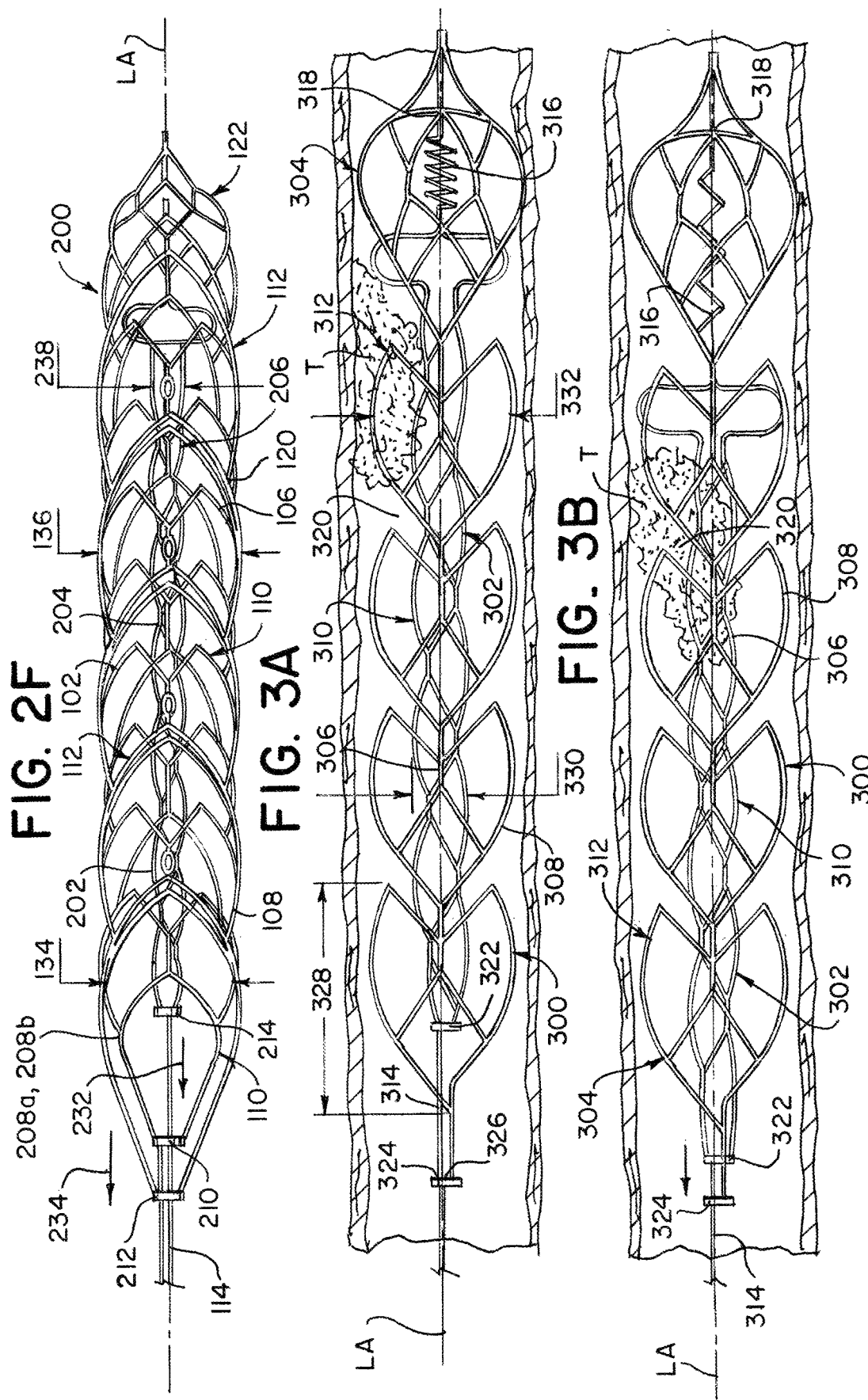

VASCULAR OBSTRUCTION RETRIEVAL DEVICE HAVING SLIDING CAGES PINCH MECHANISM

FIELD OF INVENTION

The present disclosure relates generally to devices and methods for removing blockages from blood vessels during intravascular medical treatments.

BACKGROUND

Clot retrieval devices are used in mechanical thrombectomy for endovascular intervention, often in cases where patients are suffering from conditions such as acute ischemic stroke (AIS), myocardial infarction (MI), and pulmonary embolism (PE). Acute obstructions can include a clot, misplaced devices, migrated devices, large emboli, and the like. Thromboembolism occurs when part or all of a thrombus breaks away from the blood vessel wall. This clot (now called an embolus) is then carried in the direction of blood flow. An ischemic stroke can result if the clot lodges in the cerebral vasculature. A pulmonary embolism can result if the clot originates in the venous system or in the right side of the heart and lodges in a pulmonary artery or branch thereof. Clots can also develop and block vessels locally without being released in the form of an embolus—this mechanism is common in the formation of coronary blockages.

There are significant challenges associated with designing clot retrieval devices that can deliver high levels of performance. First, there are a number of access challenges that make it difficult to deliver devices. In cases where access involves navigating the aortic arch (such as coronary or cerebral blockages) the configuration of the arch in some patients makes it difficult to position a guide catheter. These difficult arch configurations are classified as either type 2 or type 3 aortic arches with type 3 arches presenting the most difficulty.

The tortuosity challenge is even more severe in the arteries approaching the brain. For example, it is not unusual at the distal end of the internal carotid artery that the device will have to navigate a vessel segment with a 180° bend, a 90° bend, and a 360° bend in quick succession over a few centimeters of vessel. In the case of pulmonary embolisms, access is through the venous system and then through the right atrium and ventricle of the heart. The right ventricular outflow tract and pulmonary arteries are delicate vessels that can easily be damaged by inflexible or high profile devices. For these reasons it is desirable that the clot retrieval device be compatible with as low profile and flexible a guide catheter as possible.

Second, the vasculature in the area in which the clot can be lodged is often fragile and delicate. For example, neurovascular vessels can be more fragile than similarly sized vessels in other parts of the body and can be in a soft tissue bed. Excessive tensile forces applied on these vessels could result in perforations and hemorrhage. Pulmonary vessels can be larger than those of the cerebral vasculature, but are also delicate in nature, particularly more distal vessels.

Additionally, the clot can have any of a range of morphologies and consistencies. For example, the clot can be difficult to grip and improper grip can lead to fragmentation which can cause embolization. Long strands of softer clot material can also tend to lodge at bifurcations or trifurcations, resulting in multiple vessels being simultaneously occluded over significant lengths. More mature and organized clot material can be less compressible than softer fresher clot, and under the action of blood pressure it can distend the compliant vessel in which it is lodged. Furthermore, the properties of the clot can be significantly changed by the action of the devices interacting with it. In particular, compression of a blood clot can cause dehydration of the clot and can result in a dramatic increase in both clot stiffness and coefficient of friction.

Lastly, traditional clot retrieval devices employing a pinch mechanism to capture a clot can require the delivery microcatheter to be forward post deployment of the clot retrieval device in order to effectively pinch a clot using the device. However, this can add an additional step in the procedure, thereby resulting in a potentially cumbersome and non-optimal procedure. Due to the critical nature of such procedures, it can be critical to capture a clot in a timely and effective manner.

The challenges described above need to be overcome for devices to provide a high level of success in removing clot and restoring flow.

SUMMARY

It is desirable for a clot retrieval device to remove a clot from cerebral arteries in patient suffering from AIS, from coronary native or graft vessels in patients suffering from MI, and from pulmonary arteries in patients from PE and from other peripheral arterial and venous vessels in which a clot is causing at least a partial occlusion. Example devices and methods presented herein may be suitable for at least some of such procedures and/or similar procedures.

An example clot retrieval device can have a constrained delivery configuration and a clot engaging configuration and can be configured to remove a clot from a blood vessel. The device can include a first expandable framework having a first plurality of struts that form a first body and a second expandable framework having a second plurality of struts that form a second body. In the clot engaging configuration, the first body can be configured to move from a first position to a second position in relation to the second body.

The first body can have a first inner diameter and the second body can have a second inner diameter. The first inner diameter and the second inner diameter can be substantially equal.

When the first body is in the first position, the first plurality of struts and the second plurality of struts can be disengaged such that a plurality of clot reception spaces are formed.

When the first body is in the second position, the first plurality of struts and the second plurality of struts can be engaged such that an average cross-sectional area of the plurality of clot reception spaces decreases upon movement of the first body from the first position to the second position.

The first plurality of struts can include a radially extending strut and the second plurality of struts can include an eye through which the radially extending strut radially extends. The eyelet and the radially extending strut can be configured such that when the first body moves from the first position to the second position, the radially extending strut engages the eyelet to inhibit the first plurality of struts from moving, in relation to the second plurality of struts, beyond the second position. Each eyelet can be tapered.

The clot retrieval device can include a polymer coating to engage the first plurality of struts and the second plurality of struts. The polymer coating can be configured to fail, thereby allowing the first body to move from the first position to the second position.

At least one polymer membrane can be affixed to the first plurality of struts and the second plurality of struts such that the polymer membrane is disposed between the first body and the second body.

The at least one polymer membrane can be in a folded configuration when the first body is in the first position and the at least one polymer membrane can transition to a stretched configuration when the first body moves proximally to the second position.

The clot retrieval device can include a third expandable framework having a third framework of struts that form a third body. The first body and the second body can at least partially surround the third body in the clot engaging configuration.

A proximal end of the clot retrieval device can include a plurality of expanded struts that form a collar.

The third framework of struts can include at least one disconnected strut.

The third body can include a plurality of clot reception spaces. The plurality of clot reception spaces can be configured to engage the clot.

Another example clot retrieval device can have a constrained delivery configuration and a clot engaging configuration and can be configured to remove a clot from a blood vessel. The device can include an inner expandable framework, an outer expandable framework, and a spring. The inner expandable framework can be affixed to a pull wire and can include a first plurality of struts that form an inner body. The outer expandable framework can be affixed to the pull wire and can include a second plurality of struts that form an outer body at least partially surrounding the inner body. The spring can be affixed to a distal end of the pull wire and can have a compressed configuration and an elongated configuration. In the clot engaging configuration, the inner body can be configured to move from a first position to a second position in relation to the outer body such that the spring transitions from the compressed configuration to the elongated configuration.

The outer expandable framework can include a plurality of clot reception spaces that are configured to pinch the clot between the inner body and the outer body when the inner body moves from the first position to the second position.

An example method to capture a clot can include deploying a clot retrieval device proximate the clot where the clot retrieval device includes a first expandable framework forming a first body and a second expandable framework forming a second body at least partially surrounding the first body. The method can further include moving the first body in relation to the second body to pinch at least a portion of the clot between the first body and the second body and capturing one or more fragments of the clot.

Moving the first body in relation to the second body to pinch at least a portion of the clot between the first body and the second body can include applying tension to a pull wire where the pull wire is in mechanical communication with the first body.

The method can further include retracting the first body and the second body simultaneously.

The clot retrieval device can further include a third expandable framework having a third plurality of struts that form a third body. The first body and the second body can at least partially surround the third body. In such configuration, the method can further include retracting the third body in a proximal direction to engage the first body and the third body.

BRIEF DESCRIPTION OF THE DRAWINGS

FIG. 1A is a side view of an example clot retrieval device in a clot engaging configuration, in accordance with the present disclosure.

FIG. 1B is an additional side view from a different perspective of the clot retrieval device of FIG. 1A, in accordance with the present disclosure.

FIG. 1C is a cross-section view of a shaft of the clot retrieval device of FIGS. 1A and 1B, in accordance with the present disclosure.

FIG. 1D is an expanded view of the pull wire joined to a first plurality of struts of the clot retrieval device of FIGS. 1A and 1B, in accordance with the present disclosure.

FIG. 1E is an expanded view of a radially extending strut and an eyelet of the clot retrieval device of FIGS. 1A and 1B, in accordance with the present disclosure.

FIG. 1F is a side view of the clot retrieval device of FIGS. 1A and 1B upon transitioning to a clot pinching configuration, in accordance with the present disclosure.

FIG. 1G is an additional side view of the clot retrieval device in the clot pinching configuration illustrated in FIG. 1F, in accordance with the present disclosure.

FIG. 2A is a side view of an additional example clot retrieval device in a clot engaging configuration, in accordance with the present disclosure.

FIG. 2B is a cross-sectional view of a proximal portion of the clot retrieval device of FIG. 2A, in accordance with the present disclosure.

FIG. 2F is an additional side view of the clot retrieval device of FIG. 2A, in accordance with the present disclosure.

FIG. 3A illustrates an additional example clot retrieval device having a spring in a compressed configuration, in accordance with the present disclosure.

FIG. 3B illustrates the clot retrieval device of FIG. 3A where the spring is in an elongated configuration, in accordance with the present disclosure.

DETAILED DESCRIPTION

Figure 2C:
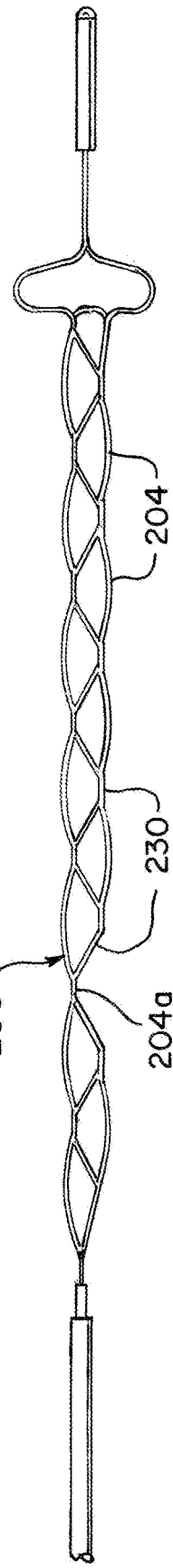
FIGS. 2C-2E illustrate examples of a third body of the clot removal device of FIG. 2A, in accordance with the present disclosure.

The design and functionality described in this application is intended to be exemplary in nature and is not intended to limit the instant disclosure in any way. Those having skill in the pertinent art will appreciate that the teachings of the disclosure may be implemented in a variety of suitable forms, including those forms disclosed herein and additional forms known to those having skill in the art pertinent.

It will be apparent from the foregoing description that, while particular embodiments of the present disclosure have been illustrated and described, various modifications can be made without departing from the spirit and scope of the disclosure. For example, while the embodiments described herein refer to particular features, the disclosure includes embodiments having different combinations of features. The disclosure also includes embodiments that do not include all of the specific features described. Specific embodiments of the present disclosure are now described in detail with reference to the figures, wherein identical reference numbers indicate identical or functionality similar elements.

The terms "distal" or "proximal" are used in the following description with respect to a position or direction relative to the treating physician. "Distal" or "distally" are a position distant from or in a direction away from the physician. "Proximal" or "proximally" or "proximate" are a position near or in a direction toward the physician.

In the following description, numerous specific details are set forth. But it is to be understood that examples of the disclosed technology can be practiced without these specific details. In other instances, well-known methods, structures, and techniques have not been shown in detail in order not to obscure an understanding of this description. References to "one embodiment," "an embodiment," "example embodiment," "some embodiments," "certain embodiments," "various embodiments," "one example," "an example," "some examples," "certain examples," "various examples," etc., indicate that the embodiment(s) and/or example(s) of the disclosed technology so described may include a particular feature, structure, or characteristic, but not every embodiment necessarily includes the particular feature, structure, or characteristic. Further, repeated use of the phrase "in one embodiment" or the like does not necessarily refer to the same embodiment, example, or implementation, although it may.

By "comprising" or "containing" or "including" or "having" is meant that at least the named compound, element, particle, configuration, or method step is present in the composition or device or method, but does not exclude the presence of other compounds, materials, particles, method steps, or configurations even if the other such compounds, material, particles, method steps, or configurations have the same function as what is named.

Throughout the specification and the claims, the following terms take at least the meanings explicitly associated herein, unless the context clearly dictates otherwise. The term "or" is intended to mean an inclusive "or." Further, the terms "a," "an," and "the" are intended to mean one or more unless specified otherwise or clear from the context to be directed to a singular form.

Unless otherwise specified, the use of the ordinal adjectives "first," "second," "third," etc., to describe a common object, merely indicate that different instances of like objects are being referred to, and are not intended to imply that the objects so described should be in a given sequence, either temporally, spatially, in ranking, or in any other manner.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 99%.

As discussed herein, a "patient" or "subject" can be a human or any animal. It should be appreciated that an animal can be a variety of any applicable type, including, but not limited to, mammal, veterinarian animal, livestock animal or pet-type animal, etc. As an example, the animal can be a laboratory animal specifically selected to have certain characteristics similar to a human (e.g., rat, dog, pig, monkey, or the like).

Accessing the various vessels within the vascular, whether they are coronary, pulmonary, or cerebral, involves well-known procedural steps and the use of a number of conventional, commercially-available accessory products. These products, such as angiographic materials and guidewires are widely used in laboratory and medical procedures. When these products are employed in conjunction with the system and methods of this disclosure in the description below, their function and exact constitution are not described in detail.

The disclosed technology can generally include a clot removal device having a sliding cage (e.g., a first body) and an outer cage (e.g., a second body) radially surrounding the sliding cage. A pull wire can be affixed to the sliding cage such that upon tension being applied to the pull wire, the sliding cage can displace proximally and independently of the outer cage. Upon the sliding cage displacing proximally, the sliding cage and the outer cage can pinch the clot. In some instances, the clot removal device can further include an inner channel (e.g., third body). The outer cage and the sliding cage can radially surround the inner channel. Upon tension being applied, the inner channel can move proximally and independently of the outer cage and sliding cage. Subsequently, the sliding cage can move proximally in relation to the outer cage and independently of the outer cage. In such configuration the sliding cage and the outer cage can further pinch the clot and the clot can thereby become further integrated within the clot removal device. Accordingly, the efficient and effective removal of a clot from a blood vessel can be performed.

Referring now to the Figures, FIGS. 1A and 1B illustrate side views of an example clot retrieval device 100 in a clot engaging configuration. The clot retrieval device 100 can include a first expandable framework 102 and a second expandable framework 104. The first expandable framework 102 can include a first plurality of struts 106 and the second expandable framework 104 can include a second plurality of struts 108.

The first expandable framework 102 and the second expandable framework 104 can be collapsible into a restraining sheath (e.g., a microcatheter) sized to traverse a clot or other obstruction. The clot retrieval device 100 can be positioned proximate the clot in a blood vessel. Optionally, the clot retrieval device 100 can traverse the clot such that a portion of the clot remove device 100 is forward in relation to the clot. The first expandable framework 102 and the second expandable framework 104 can each be configured to self-expand upon release from the restraining sheath. Upon release, the clot retrieval device 100 can transition from a constrained delivery configuration to the clot engaging configuration such that the clot retrieval device 100 can be subsequently used to facilitate clot removal, flow restoration, and or fragmentation protection.

Upon transitioning to the clot engaging configuration, the first plurality of struts 106 of the first expandable framework 102 can expand to form a first body 110. Similarly, the second plurality of struts 108 of the second expandable framework 104 can expand to form a second body 112. The second body 112 can at least partially radially surround the first body 110. Optionally, the second body 112 can entirely radially surround the first body 110.

Both the first expandable framework 102, including the first plurality of struts 106, and the second expandable framework 104, including the second plurality of struts 108, can preferably be made from a material capable of recovering its shape automatically once released from the constrained delivery configuration. A super-elastic or pseudo-elastic material such as Nitinol or an alloy of similar properties is particularly suitable. The material can have a high recoverable strain sufficient to resiliently collapse and expand as described herein. The material could be in many forms such as wire or strip or sheet or tube. A particularly suitable manufacturing process is to laser cut a Nitinol tube and then heat set and electropolish the resultant structure to create a framework of struts and connecting elements. For example, the first expandable framework 102 and the second expandable framework 104 can each be laser cut from a Nitinol tube having an outer diameter of approximately 0.40 millimeters. Each of the cells in the first and second expandable frameworks 102, 104 can be any of a range of shapes as understood by a person skilled in the pertinent art according to the teachings disclosed herein. The first and second expandable frameworks 102, 104 can be rendered visible under fluoroscopy through the addition of alloying elements or through a variety of other coatings or marker bands. For instance, the first and second expandable frameworks 102, 104 can include material and/or markers with radiopaque material including, but not limited to Barium Sulphate, Bismuth SubCarbonate, Barium OxyChloride, Gold, Tungsten, Platinum, Iridium, Tantalum, and alloys thereof. Specifically, in some examples, the first and second expandable frameworks 102, 104 can include radiopaque markers having an Iridium alloy, and more specifically a Platinum-Iridium alloy.

As illustrated in FIGS. 1A and 1B, in the clot engaging configuration, the first body 110 and the second body 112 can each have a substantially cylindrical shape. Further, the first body 110 can have a first inner diameter 134 and the second body 112 can have a second inner diameter 136. The first inner diameter 134 can be approximately the same as the second inner diameter 136 such that the first body 110 and the second body 112 can substantially align with each other. By way of example, the first inner diameter 134 of the first body can be approximately 4.75 millimeters and the second inner diameter 136 can be approximately 5 millimeters. Because the first body 110 and the second body 112 have substantially equal inner diameters 132, 134, the first body 110 can exert an outward force onto the second body 112 in the clot engaging configuration.

FIGS. 1A and 1B illustrate the first body 110 and the second body 112 in a first position. The first plurality of struts 106 can form a first plurality of scaffolding segments 138a having closed cells and the second plurality of struts 108 of the second body 112 can form a second plurality of scaffolding segments 138b also having closed cells. The first plurality of scaffolding segments 138a and the second plurality of scaffolding segments 138b can be substantially aligned with each other. A gap can be formed between each scaffolding segment of the first and second plurality of scaffolding segments 138a, 138b. Such gap can be a clot reception space 120 configured to receive a clot. Portions of the clot can enter such clot reception spaces 120, thereby being captured by the clot retrieval device 100, upon the first body 110 moving from the first position to a second position in relation to the second body 112 as further discussed herein.

A distal end of the first body 110 and the second body 112 can form a distal basket 122. The distal basket 122 can have a substantially conical shape and can mitigate and/or prevent captured fragments of a clot from migrating out of the clot retrieval device 100.

As further illustrated in FIGS. 1C and 1D, a proximal end of the clot retrieval device 100 can include a shaft 132 including a pull wire 114 surrounded by an outer sheath 116. Proximal struts of the first plurality of struts 106 can be affixed to the pull wire 114, as illustrated in FIG. 1D. The pull wire 114 can be made of stainless steel, MP35N, Nitinol, or other material of suitably high modulus and tensile strength. The pull wire 114 can preferably have a solid core but can also have a hollow core. The first plurality of struts 106 of the first body 110 can be affixed to the pull wire 114 at a joint 130 via welding, bonding, by virtue of being cut from a contiguous tube, or other means of attachment. The joint 130 can be created at the approximate location of attachment of the proximal struts of the first plurality of struts 106 and the pull wire 114. Such joint 130 can inhibit unintended movement beyond a desired position when the first body 110 moves in relation to the second body 112 as further discussed herein. The second plurality of struts 108 of the second body 112 can be joined to the outer sheath 116, via welding, bonding, or the second body 112 can be formed using the same Nitinol or other material tubing of the outer sheath 116. Because the first body 110 and the second body 112 are affixed to independent portions of the shaft 132 (e.g., the pull wire 114 and the outer sheath 116, respectively), the first body 110 and the second body 112 can move independently of each other upon tension being applied to the pull wire 114 as further discussed herein.

FIG. 1E illustrates an expanded view of the substantially aligned first body 110 and the second body 112 and including an optional radially extending strut 126 and eyelet 124 to inhibit range of sliding movement between the first body 110 and the second body 112. As illustrated, the second body 112 can radially surround the first body 110 such that the second plurality of struts 108 are exterior to the first plurality of struts 106. The second plurality of struts 108 can further include one or more eyelets 124, and the first plurality of struts 106 can include one or more radially extending "connector" struts each extending through a respective eyelet 124. Each eyelet 124 can have an elongated or alternatively shaped opening. By way of example, the eyelet 124 can be substantially ovular, circular, rectangular, or the like. In some example, the eyelet 124 can be substantially tapered.

FIGS. 1F and 1G illustrate side views of the clot retrieval device 100 in a clot pinching configuration in which the first body 110 moves (e.g., slides) from the first position as illustrated in FIGS. 1A and 1B to a second position in relation to the second body 112. The pull wire 114 can be pulled in the proximal direction to apply tension. The tension can cause the first body 110 to move from the first position (FIGS. 1A and 1B) to the second position (FIGS. 1F and 1G) in relation to the second body 112. Accordingly, the first body 110 can slide from the first position to the second position in relation to the second body 112 such that the first body 110 and the second body 112 become engaged with one another. For example, the first body 110 can slide less than approximately 5 millimeters in relation to the second body 112. Optionally, the first body 110 can slide less than approximately 4 millimeters in relation to the second body 112. Optionally, the first body 110 can slide less than approximately 2 millimeters in relation to the second body 112. Optionally, the first body 110 can slide less than approximately 0.5 millimeters in relation to the second body 112. When the first body 110 moves from the first position to the second position and the device 100 includes one or more radially extending struts 126 through respective eyelets 124 as illustrated in FIG. 1E, the radially extending struts 126 can engage with the eyelets 124, thereby allowing the first body 110 and the second body 112 to become engaged with one another. Further, the eyelet 124 can inhibit the first body 110 from moving, in relation to the second body 112, beyond the second position, as the eyelet 124 can restrict the radially extending strut 126 from moving too far in the proximal direction.

Additionally, or alternatively, the first expandable framework 102 and the second expandable framework 104 can be coated with a polymer coating (e.g., parylene) to temporarily hold the first body 110 in the first position in relation to the second body 112. Upon the pull wire 114 being pulled in the proximal direction, the polymer coating can fail such that the first body 110 can move from the first position to the second position in relation to the second body 112. Aspiration can be applied in order to remove particulate from the failed polymer coating.

Additionally, or alternatively, a shape memory effect of the first body 110 and the second body 112 can be used to cause automatic displacement of the first body 110 after a predetermined time period has lapsed. For example, the second plurality of struts 108 of the second expandable framework 104 can be heat treated locally to increase the austenite finish temperature to a range greater than a typical body temperature during a stroke or other critical body occurrence. The second plurality of struts 108 can expand upon being re-sheathed then be heated to the austenite finish temperature by electrical current. Upon the austenite finish temperature being reached, the first body 110 can automatic move (e.g., slide) in relation to the second body 112 from the first position to the second position, such that the clot can be pinched between the first body 110 and the second body 112.

The pull wire 114 can be pulled in the proximal direction such that the first body 110 moves (e.g., slides) in the proximal direction until the proximal struts of the first plurality of struts 106 encounter the joint 130 positioned proximate the shaft 132. As such, the joint 130 can act as a mechanism to prevent undesired movement beyond the second position. As the first body 110 moves from the first position to the second position the average cross-sectional area of the plurality of clot reception spaces 120 can decrease (e.g., at least partially close). For example, the plurality of clot reception spaces 120 can at least partially close when the first plurality of scaffolding segments 138a slide in relation to the second plurality of scaffolding segments 138b such that the first plurality of scaffolding segment 138a become disposed across the clot reception spaces 120. Thereby, the clot can be pinched between the first body 110 and the second body 112. Pinching of the clot can prevent the clot from migrating out of the clot retrieval device 100, particularly upon retraction of the clot retrieval device 100, as the pinch can increase the grip of the clot retrieval device 100 as compared to other clot retrieval devices, particularly fibrin rich clots. Accordingly, the clot retrieval device 100 can ensure effective and efficient removal of the clot from the patient.

As illustrated in FIGS. 1F and 1G, the clot retrieval device 100 can include a polymer membrane 128 disposed between the first body 110 and the second body 112. The polymer membrane 128 (e.g., elastic membrane) can be configured to transition from a folded configuration when the first body 110 is in the first position such that the first body 110 and the second body 112 are disengaged to a stretched configuration upon the first body 110 moving from the first position to the second position. The polymer membrane 128 can thereby function to limit lateral movement of the first body 110 in relation to the second body 112 in addition to, or as an alternative to the radially extending strut 126 and eyelet 124 illustrated in FIG. 1E. The polymer membrane 128 can be formed by threading microfibers through the eyelets 124 of the second body 112, and/or the polymer membrane 128 can be formed by hooking the polymer membrane 128 into the eyelets 124. The polymer membrane 128 can prevent the clot from migrating out of the clot retrieval device 100 once the clot has been pinched between the first body 110 and the second body 112. Although FIGS. 1F and 1G illustrate the polymer membrane 128 in one location, it is contemplated that the clot retrieval device 100 can include additional polymer membranes 128 over multiple locations. For example, the clot retrieval device 100 can include a first polymer membrane proximate the distal basket of the 122 and a second polymer membrane proximate the shaft 132.

FIG. 2A illustrates an additional example clot retrieval device 200. As discussed above with reference to the clot retrieval device 100 illustrated in FIGS. 1A through 1G, the clot retrieval device 200 can similarly include the first expandable framework 102 including a first plurality of struts 106 and a second expandable framework 104 including a second plurality of struts 108. Upon the clot retrieval device 200 being deployed from a restraining sheath (e.g., microcatheter) and transitioning from a constrained delivery configuration to a clot engaging configuration, the first plurality of struts 106 of the first expandable framework 102 can self-expand to form the first body 110 and the second plurality of struts 108 of the second expandable framework 104 can self-expand to form the second body 112. The first body 110 and the second body 112 can be substantially cylindrical. Additionally, the first body 110 and the second body 112 can have substantially equal inner diameters 134, 136. As such, and as discussed above, the plurality of scaffolding sections 138a, 138b of the first body 110 and the second body 112 can be substantially aligned with one another.

In contrast to the clot retrieval device 100 illustrated in FIGS. 1A through 1G, the clot retrieval device 200 can further include a third expandable framework 202 having a third plurality of struts 204. Upon the clot retrieval device 200 being deployed from the restraining sheath, the third plurality of struts 204 of the third expandable framework 202 can self-expand to form a third body 206. The third body 206 can be substantially porous. Further, the third body 206 can similarly be substantially cylindrical and can have an inner diameter 238 that is less than the inner diameter 134 of the first body 110 and the inner diameter 136 second body 112. Thereby, the first body 110 and the second body 112 can radially surround the third body 206. Optionally, the third body 206 can have an inner diameter 238 that is approximately half (½) the size of the inner diameter 134 of the first body 110 and inner diameter 136 of the second body 112. Optionally, the third body 206 can have an inner diameter 238 that is approximately three quarters (¾) the size of the inner diameter 134 of the first body 110 and the inner diameter 136 of the second body 112. The third expandable framework 202 can be preferably made from a material capable of recovering its shape automatically once released from a constricted delivery configuration. A super-elastic or pseudo-elastic material such as Nitinol or an alloy of similar properties is particularly suitable. The material can have a high recoverable strain sufficient to resiliently collapse and expand as described herein. The material could be in many forms such as wire or strip or sheet or tube. A particularly suitable manufacturing process is to laser cut a Nitinol tube and then heat set and electropolish the resultant structure to create a framework of struts and connecting elements. Optionally, the third expandable framework 202 can be laser cut from a Nitinol tube.

As discussed above with reference to the clot retrieval device 100, the first body 110 can include a first plurality of scaffolding segments 138*a* and the second body 112 can include a second plurality of scaffolding segments 138*b*. The first and second plurality of scaffolding segments 138*a*, 138*b* can substantially align with one another. A gap can be formed between each scaffolding segment of the first plurality and second plurality of scaffolding segments 138*a*, 138*b*. Such gap can be a clot reception space 120 configured to receive at least a portion of a clot upon the clot retrieval device 200 transitioning to a clot pinching configuration as further described herein. The configuration of the third body 206 can similarly create additional clot reception spaces 230 as further discussed herein.

The distal end of the clot retrieval device 200 can include the distal basket 122. The distal basket 122 can have a substantially conical shape and can mitigate captured fragments of a clot from migrating out of the clot retrieval device 200.

As further illustrated in FIG. 2B, a plurality of expanded struts 208*a*, 208*b* can be formed from the shaft 216 of the first body 110. For example, the shaft 216 of the first body 110 can be a tube (e.g., Nitinol tube) and the two expanded struts 208*a*, 208*b* can be formed (e.g., laser cut) from such tube. The shaft 216 of the first body 110 can be a hollow tube sized to receive the pull wire 114. As such, the pull wire 114 can extend through the shaft 216 of the first body 110. The plurality of expanded struts 208*a*, 208*b* can facilitate improved pinching when the clot retrieval device 200 transitions to the clot pinching configuration. Optionally, the plurality of expanded struts 208*a*, 208*b* can be used to allow re-expansion of the third body 206 to stabilize the clot if an effective pinch is not formed upon the clot retrieval device 200 transitioning to the clot pinching configuration. A shaft 222 of the second body 112 can surround the shaft 216 of the first body 110 and the pull wire 114. The shaft 222 of the second body 112 can be a tube (e.g., a Nitinol tube). Proximal struts 224 of the second body 112 can extend from a distal end of the shaft 222 of the second body 112. The proximal struts 224 can be the most proximal struts of the second expandable framework 104. A proximal end of a shaft 218 of the third body 206 can be affixed to a distal end of the pull wire 114. The shaft 218 of the third body 206 can be a solid core tube. A joint 220 (e.g. weld joint) can be formed where the shaft 218 of the third body 206 is affixed to the pull wire 114 and where the shaft 216 of the first body 110 forms the expanded struts 208*a*, 208*b*. Proximal struts 226 of the third body 206 can extend from a distal end of the shaft 218 of the third body 206. The proximal struts 226 can be the most proximal struts of the third expandable framework 202.

Figure 2D:
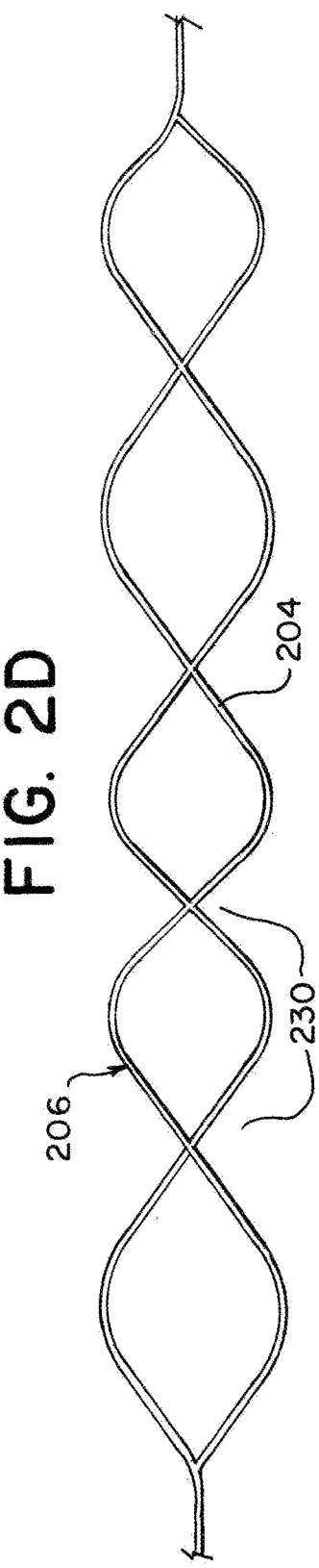
Figure 2E:
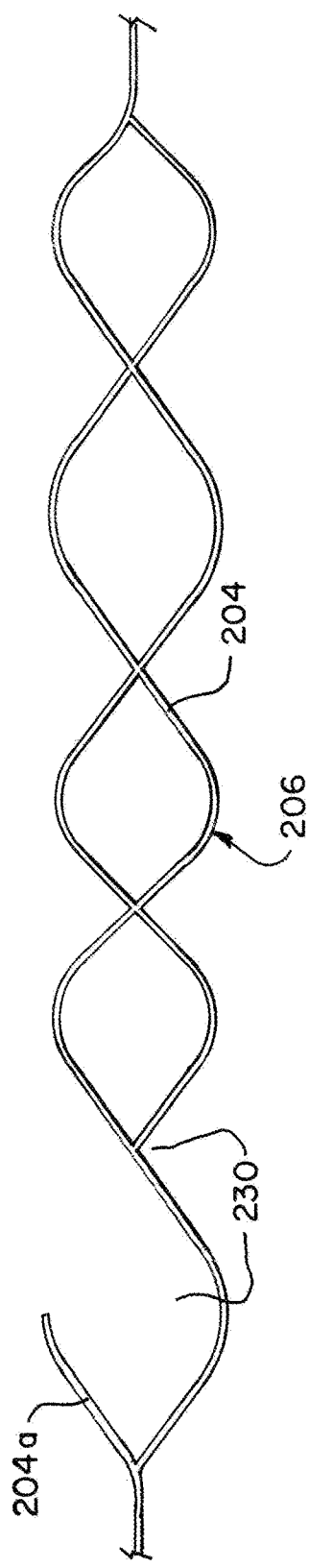

FIGS. 2C through 2E illustrate various configurations of the third body 206. In FIGS. 2C through 2E, the third plurality of struts 204 can be configured to form a substantially cylindrical body of interconnected struts. The third plurality of struts 204 can be interconnected with one another such that the third plurality of struts form a majority of closed cells. The third plurality of struts 204 can be configured to form closed cells of differing sizes and shapes. Optionally, the closed cells can be sized according to the content of the clot to be captured (e.g., based on how soft and/or fibrin rich the clot to be captured is). As illustrated in FIGS. 2C through 2E, the third body 206 can further include a plurality of clot reception spaces 230. The size of each clot reception space 230 can be based on the configuration of the third plurality of struts 204. Optionally, as illustrated in FIGS. 2C and 2E, the third plurality of struts 204 can include at least one disconnected strut 204 a. The disconnected strut can form an open cell. Such open cell can form a larger clot reception space 230, and thereby facilitate migration of the clot into the third body 206. Optionally, the third plurality of struts 204 can include a plurality of disconnected struts 204 a such that a majority of the cells are open cells. The third body 206 can serve two primary functions. For example, the third body 206 can facilitate allowing blood to pass through so that there is at least partial blood flow through the blood vessel as a clot is being captured and withdrawn by the clot retrieval device 200. Additionally, upon the clot retrieval device 200 being deployed, a clot can become partially integrated into the clot reception spaces 120 of the first body 110 and the second body 112. Upon the third body 206 moving (e.g., sliding) in relation to the first body 110 and the second body 112, the third body 206 can interact with the clot, thereby promoting further integration of the clot between the first body 110 and the second body 112 prior to forming a pinch.

FIG. 2F illustrates an additional side view of the clot retrieval device 200. As illustrated in FIG. 2F, the first body 110 can include a first collar 210, the second body 112 can include a second collar 212, and the third body 206 can include a third collar 214. Each collar 210, 212, 214 can facilitate moving (e.g., sliding) the third body 206 in relation to the first body 110 and the second body 112 and subsequently moving (e.g., sliding) the first body 110 in relation to the second body 112 to pinch at least a portion of a clot. The pull wire 114 can be affixed to the third body 206 and can be threaded through each collar 210, 212, 214 such that upon the pull wire 114 being pulled in the proximal direction, the clot retrieval device 200 can move (e.g., slide) from a first position to a second position and subsequently from a second position to a third position.

Figure 2G:
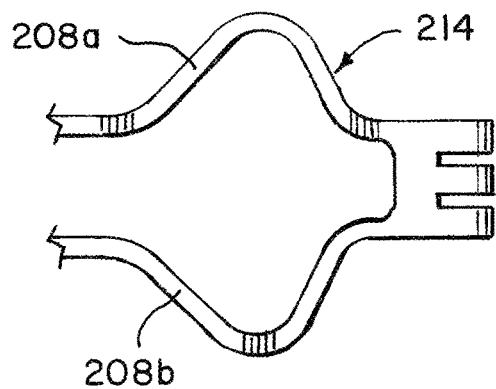
FIG. 2G illustrates an example third collar of the clot removal device of FIG. 2A, in accordance with the present disclosure.

FIG. 2G illustrates an example third collar 214. The third collar 214 can be disposed where the expanded struts 208*a*, 208*b* conjoin. The third collar 214 can be laser cut in a particular design to facilitate pinching the clot upon the clot retrieval device 200 moving from the first position to the second position and subsequently from the second position to the third position.

In order to pinch the clot using the clot retrieval device 200, the pull wire 114 can be pulled in a proximal direction. Such tension can cause the third body 206 to move (e.g., slide) in relation to the first body 110 and the second body 112 causing the clot retrieval device 200 to transition from the first position to the second position, as indicated by a first arrow 232. For example, the third body 206 can slide less than approximately 5 millimeters in relation to the first body 110 and the second body 112. Optionally, the third body 206 can slide less than approximately 4 millimeters in relation to the first body 110 and the second body 112. Optionally, the third body 206 can slide less than approximately 2 millimeters in relation to the first body 110 and the second body 112. Optionally, the third body 206 can slide less than approximately 0.5 millimeters in relation to the first body and the second body 112.

Upon the third body 206 moving in relation to the first body 110 and the second body 112, at least a portion of the clot can be pinched between the third body 206 and the first body 110 and the second body 112 to cause the portions of the clot to migrate inside the first body 110 and the second body 112. Additionally, upon the third body 206 moving from the first position to the second position, the third body 206 can become engaged with the first body 110 as the third collar 214 becomes engaged with the first collar 210. When the third collar 214 and the first collar 210 become engaged, the pull force can be transferred to the first body 110, thereby allowing for further displacement.

Subsequently, the first body 110 can move (e.g., slide) in relation to the second body 112 such that the clot retrieval device 200 transitions from the second position to the third position, as indicated by a second arrow 234. For example, the first body 110 can slide less than approximately 5 millimeters in relation to the second body 112. Optionally, the first body 110 can slide less than approximately 4 millimeters in relation to the second body 112. Optionally, the first body 110 can slide less than approximately 2 millimeters in relation to the second body 112. Optionally, the first body 110 can slide less than approximately 0.5 millimeters in relation to the second body 112.

Upon the first body 110 moving from the second position to the third position, the first body 110 engaged with the third body 206 can become engaged with the second body 112 causing an average cross-sectional area of the plurality of clot reception spaces 120 to decrease (e.g., at least partially close). Thereby, at least a portion of the clot can be further pinched. The portions of the clot can be pinched between the first body 110 and the second body 112 and, additionally, the third body 206. Accordingly, the portions of the clot can further migrate inside third body 206. As such, the portions of the clot can further migrate into the clot reception spaces 230 of the third body 206. Upon transitioning to the third position, the expanded struts 208a, 208b can become resheathed as the first collar 210 becomes engaged with the second collar 212. When the first collar 210 becomes engaged with the second collar 212, the pull force can be transferred to the second body 112. Accordingly, the first body 110, the second body 112, and the third body 206, including the captured clot or portions thereof, can be removed simultaneously from the patient's vasculature.

Optionally, the clot retrieval device 200 can include a seal that allows the clot retrieval device 200 to maintain a pinch even if the physician stops applying tension. For example, the clot retrieval device 200 can include a seal disposed proximate the weld joint 220. The seal can maintain the clot retrieval device 200 in place using friction. As such, the seal can create enough static friction such that the clot removal device 200 does not displace when a physician stops applying tension while also ensuring the static friction is not too high that a user cannot overcome such static friction when manipulating the clot retrieval device 200 during retrieval of the clot and removal of the clot retrieval device 200 from a patient.

FIGS. 3A and 3B illustrate an additional example clot retrieval device 300. The clot retrieval device 300 can have a constrained delivery configuration and a clot engaging configuration and can be configured to remove a clot (e.g., thrombus) T from a blood vessel. The clot removal device 300 can be in the constrained delivery configuration when the clot removal device 300 is positioned within a restraining sheath (e.g., microcatheter). Upon the restraining sheath being retracted, the clot removal device 300 can transition to the clot engaging configuration. The clot retrieval device 300 can include an inner expandable framework 302 and an outer expandable framework 304. The inner expandable framework 302 can include an inner plurality of struts 306 that self-expand to form an inner body 310 upon the clot retrieval device 300 transitioning from the constrained delivery configuration to the clot engaging configuration. Similarly, the outer expandable framework 304 can include an outer plurality of struts 308 that self-expand form an outer body 312 upon the clot retrieval device 300 transitioning from the constrained delivery configuration to the clot engaging configuration. The inner expandable framework 302 and the outer expandable framework 304 can be preferably made from a material capable of recovering its shape automatically once released from a constricted delivery configuration and further include the additional characteristics as described above with reference to the first expandable framework 102 and the second expandable framework 104.

The inner body 310 and the outer body 312 can have different inner diameters 330, 332 and/or configurations. For example, the inner body 310 can have a smaller inner diameter 330 than the inner diameter 332 of the outer body 312, as such the outer body 312 can radially surround the inner body 310. Optionally, the inner diameter 330 of the inner body 310 can be approximately half of the size of the inner diameter 332 of the outer body 312. Optionally, the inner diameter 330 of the inner body 310 can be approximately ¾ of the size of the inner diameter 332 of the outer body 312. As illustrated in FIG. 3A, the differing diameters 330, 332 and shape configurations of the inner body 310 and the outer body 312 can form a plurality of clot reception spaces 320 configured to engage with a clot T. For example, the outer body 312 can include a plurality of scaffolding sections. A clot reception space 320 can be formed between each scaffolding section 338 of the plurality of scaffolding sections. Additionally, the inner body 310 can have a substantially "S" wave shape. Such "S" wave shape can facilitate pinching and capturing the clot upon the inner body 310 moving in relation to the outer body 312, and upon capturing the clot, preventing the captured clot from migrating out of the clot retrieval device 300.

The inner body 310 and the outer body 312 can each be affixed to a pull wire 314. The pull wire 314 can include a first stopper 322 and a second stopper 324 at a proximal end 326 of the pull wire. The first stopper 322 can be disposed distally in relation to the second stopper 324.

A spring 316 can be affixed to a distal end 318 of the pull wire 314. The spring 316 can be configured to transition from a compressed configuration and an elongated configuration upon actuation. The spring 316 can be configured to maintain a central position of the inner body 310 within the outer body 312. In the previously illustrated clot retrieval devices 100, 200 because the first body 110 has an approximately equal inner diameter 134 to the second body 112, the first body 110 resides centrally within the second body 112 because of outward force from the first body 110 onto the second body 112. When the inner body 310 has a substantially smaller inner diameter 330 than the outer body 312 as illustrated in FIGS. 3A and 3B, a distal portion of the inner body 310 can radially deflect with respect to the outer body 312 but for the spring 316 which inhibits the distal portion from deflecting. The spring 316 can further function to hold the device 300 in a first position when the pull wire 314 is not under tension.

As illustrated in FIG. 3A, the clot retrieval device 300 can be positioned proximate to the clot T. At least a portion of the clot retrieval device 300 can traverse the clot T such that a distal end of the clot retrieval device 300 can be forward in relation to the clot T. The pull wire 314 can be pulled in a proximal direction causing the inner body 310 to move (e.g., slide) from the first position to the second position in relation to the outer body 312.

FIG. 3B illustrates the clot retrieval device 300 transitioning to a clot pinching configuration upon the inner body 310 moving from the first position to the second position. The pull wire 314 can be pulled in the proximal direction until the first stopper 322 is proximate and/or engages (e.g., touches or becomes within a predetermined distance of the second stopper 324) the second stopper 324, as such the second stopper 324 can serve as an indicator of when to stop applying tension to the pull wire 314 and/or gradually weaken the amount of tension being applied to the pull wire 314. When the pull wire 314 is pulled in the proximal direction, the spring 316 can be actuated, causing the spring 316 to transition from the compressed configuration to the elongated configuration. When the spring 316 transitions to the elongated configuration, the inner body 310 can move from the first position to the second position. Such movement from the first position to the second position can cause the average cross-sectional area of the clot reception spaces 320 to decrease (e.g., at least partially close), thereby pinching the clot T between the inner body 310 and the outer body 312. Upon pinching the clot T between the inner body 310 and outer body 312, the inner body 310 and the outer body 312, including the clot T, can be retracted into the restraining sheath (e.g., microcatheter), and subsequently the clot retrieval device 300 can be removed from the patient.

Figure 4:
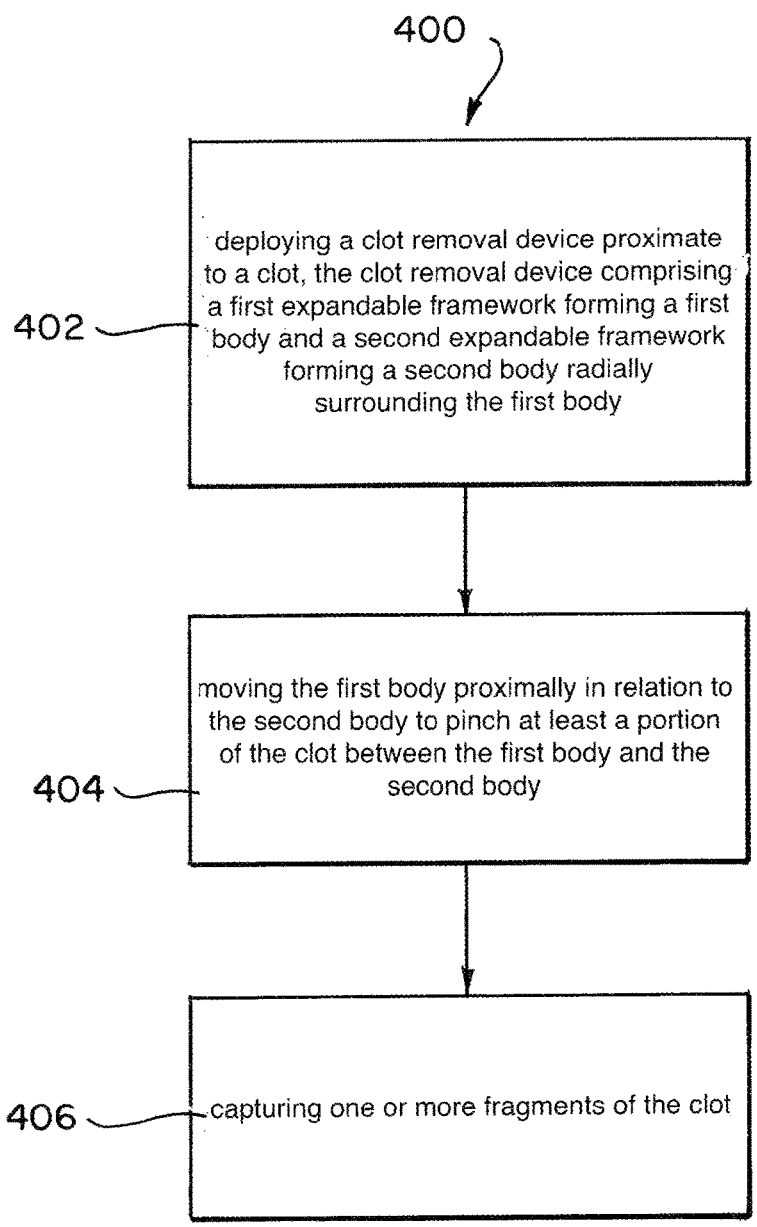
FIG. 4 is a flow diagram outlining a method of capturing a clot using the clot retrieval device of FIGS. 1A through 1G.

FIG. 4 illustrates a flow diagram outlining a method 400 of capturing a clot using the clot retrieval device 100 illustrated in FIGS. 1A through 1G. The method 400 can include deploying 402 the clot retrieval device 100 proximate to the clot. As discussed herein, the clot retrieval device 100 can include a first expandable framework 102 and a second expandable framework 104. Upon deploying the clot retrieval device 100, the clot retrieval device 100 can transition from a constrained delivery configuration to a clot engaging configuration and the first expandable framework 102 can expand to form a first body 110 while the second expandable framework 104 can expand to form a second body 112 that radially surrounds the first body 110. The first body 110 and the second body 112 can have substantially the same inner diameter 134. 136, such that the first body 110 and the second body 112 substantially radially align with one another.

The method 400 can further include moving 404 (e.g., sliding) the first body 110 proximally in relation to the second body 112 to pinch at least a portion of the clot between the first body 110 and the second body 112 such that the clot removal device 100 transitions to a clot pinching configuration. By way of example, tension can be applied to the pull wire 114 until the first body 110 encounters the joint 130. As the pull wire 114 is pulled in the proximal direction, the first body 110 can move in the proximal direction in relation to the second body 112, thereby pinching at least a portion of the clot between the first body 110 and the second body 112.

The method 400 can further include capturing 406 one or more fragments of the clot.

Additionally, the method 400 can include retracting the first body 110 and the second body 112 simultaneously, as the first body 110 and the second body 112 become engaged upon the first body 110 moving in relation to the second body 112. Similarly, upon the first body 110 and the second body 112 being retracted into a restraining sheath, the restraining sheath can be removed from a patient's vasculature.

Figure 5:
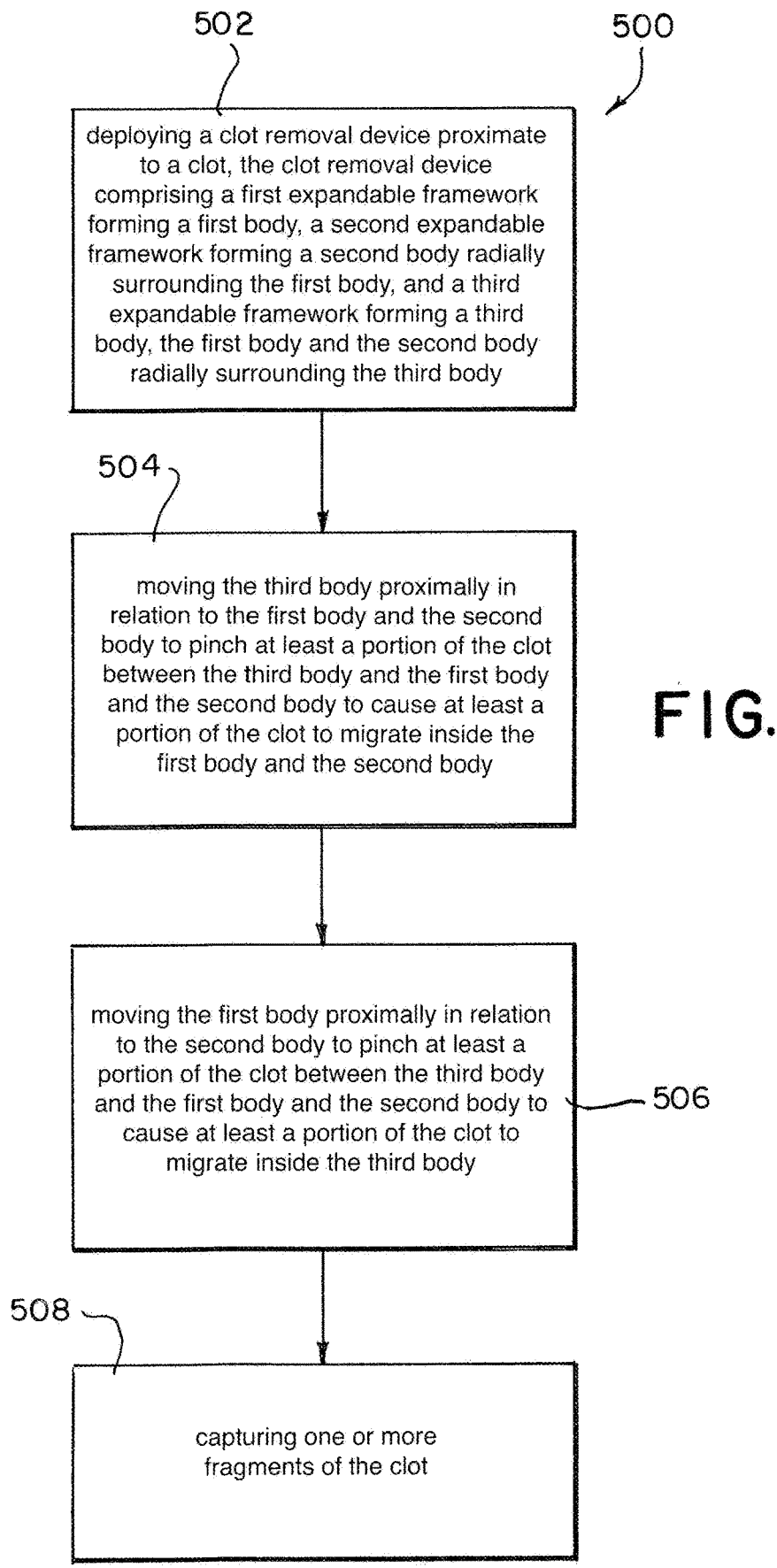
FIG. 5 is a flow diagram outlining a method of capturing a clot using the clot retrieval device of FIGS. 2A through 2G.

FIG. 5 illustrates a flow diagram outlining a method 500 of capturing a clot using the clot retrieval device 200 illustrated in FIGS. 2A through 2F. The method 500 can include deploying 502 the clot retrieval device 200 proximate to the clot. As discussed herein, the clot retrieval device 100 can include a first expandable framework 102, a second expandable framework 104, and a third expandable framework 202. Upon deploying the clot retrieval device 200, the clot retrieval device 200 can transition from a constrained delivery configuration to a clot engaging configuration and the first expandable framework 102 can expand to form a first body 110 while the second expandable framework 104 can expand to form a second body 112 that radially surrounds the first body 110. The first body 110 and the second body 112 can have substantially the same inner diameter 134. 136, such that the first body 110 and the second body 112 can substantially align with each other. Similarly, the third expandable framework 202 can expand to form the third body 206. The first body 110 and the second body 112 can radially surround the third body 206, as the third body 206 can have a smaller inner diameter 238 as compared to the first body 110 and the second body 112.

The method 500 can further include moving 504 (e.g., sliding) the third body 206 in relation to the first body 110 and the second body 112 to pinch at least a portion of the clot between the third body 206 and the first body 110 and the second body 112 such that the clot removal device 200 transitions to a clot pinching configuration. As such, at least a portion of the clot can migrate into the first body 110 and the second body 112. Upon moving the third body 206 in relation to the first body 110 and the second body 112, the third body 206 can become engaged with the first body 110.

The method 500 can further include moving 506 (e.g., sliding) the first body 110 proximally in relation to the second body 112 to further pinch at least a portion of the clot between the third body 206 and the first body 110 and the second body 112. As the first body 110 moves in relation to the second body 112, the average cross-sectional area of the clot reception spaces 120 can decrease, thereby pinching at least a portion of clot and preventing and/or mitigating the captured portions of the clot from migrating back out of the clot retrieval device 200. Upon pinching the clot, at least a portion of the clot can migrate inside the third body 206. When at least a portion of the clot is within third body 206, the potential for the portions of the captured clot to migrate back out of the clot retrieval device 200 can decrease.

The method 500 can further include capturing 508 one or more fragments of the clot.

Additionally, the method 500 can include simultaneously retracting the first body 110, the second body 112, and the third body 206. Upon being retracted into a delivery microcatheter, the delivery microcatheter can be removed from a patient's vasculature, and thus, the clot can be removed effectively and efficiently from the patient's vasculature.

Certain examples and implementations of the disclosed technology are described above with reference to block and flow diagrams according to examples of the disclosed technology. It will be understood that one or more blocks of the block diagrams and flow diagrams, and combinations of blocks in the block diagrams and flow diagrams, respectively. Likewise, some blocks of the block diagrams and flow diagrams do not necessarily need to be performed in the order presented, can be repeated, or do not necessarily need to be performed at all, according to some examples or implementations of the disclosed technology. It is also to be understood that the mention of one or more method steps does not preclude the presence of additional method steps or intervening method steps between those steps expressly identified. Additionally, method steps from one process flow diagram or block diagram can be combined with method steps from another process diagram or block diagram. These combinations and/or modifications are contemplated herein.

What is claimed is:

1. A clot retrieval device comprising a constrained delivery configuration and a clot engaging configuration and being configured to remove a clot from a blood vessel, the device comprising:

a first expandable framework comprising a closed distal end, a closed proximal end, and a first plurality of struts forming a substantially cylindrical first body comprising a plurality of cells having two or more different shapes;

a second expandable framework comprising a closed distal end, a closed proximal end, and a second plurality of struts forming a substantially cylindrical second body comprising a plurality of cells having two or more different shapes, a length of the second body at least partially surrounding and substantially aligned with a length of the first body; and a third expandable framework comprising a third plurality of struts forming a third body, the first body and the second body at least partially surrounding the third body in the clot engaging configuration, wherein in the clot engaging configuration, the first body is configured to move proximally from a first position to a second position in relation to the second body to compress at least a portion of the clot between the plurality of cells of the first body and the plurality of cells of the second body, and wherein the third body is configured to move in relation to the first body and the second body.

2. The clot retrieval device of claim 1, wherein the first body has a first inner diameter and the second body has a second inner diameter, the first inner diameter and the second inner diameter being substantially equal.

3. The clot retrieval device of claim 1, wherein when the first body is in the first position, the first plurality of struts and the second plurality of struts are disengaged such that a plurality of clot reception spaces are formed.

4. The clot retrieval device of claim 3, wherein when the first body is in the second position, the first plurality of struts and the second plurality of struts are engaged such that an average cross-sectional area of the plurality of clot reception spaces decreases upon movement of the first body from the first position to the second position.

5. The clot retrieval device of claim 1, wherein the first plurality of struts comprises at least one radially extending strut and the second plurality of struts comprises at least one eyelet through which the at least one radially extending strut radially extends, the at least one eyelet and the at least one radially extending strut being configured such that when the first body moves from the first position to the second position, the at least one radially extending strut engages the at least one eyelet to inhibit the first plurality of struts from moving, in relation to the second plurality of struts, beyond the second position.

6. The clot retrieval device of claim 5, wherein each eyelet is tapered.

7. The clot retrieval device of claim 1, further comprising a polymer coating to engage the first plurality of struts and the second plurality of struts, the polymer coating configured to fail to allow the first body to move from the first position to the second position.

8. The clot retrieval device of claim 1, further comprising at least one polymer membrane, wherein a first polymer membrane is affixed to the first plurality of struts and the second plurality of struts such that the first polymer membrane is disposed between the first body and the second body.

9. The clot retrieval device of claim 8, wherein the first polymer membrane is in a folded configuration when the first body is in the first position and the first polymer membrane transitions to a stretched configuration when the first body moves proximally to the second position.

10. The clot retrieval device of claim 1, wherein a proximal end of the clot retrieval device includes a plurality of expanded struts that form a collar.

11. The clot retrieval device of claim 1, wherein the third plurality of struts includes at least one disconnected strut.

12. The clot retrieval device of claim 1, wherein the third body comprises a plurality of clot reception spaces, the plurality of clot reception spaces configured to engage the clot.

13. A clot retrieval device comprising a constrained delivery configuration and a clot engaging configuration and being configured to remove a clot from a blood vessel, the device comprising:

an inner expandable framework affixed to a pull wire and comprising a closed distal end, a closed proximal end, and an inner plurality of struts forming a substantially cylindrical inner body comprising a plurality of cells having two or more different shapes;

an outer expandable framework affixed to the pull wire and comprising a closed distal end, a closed proximal end, and an outer plurality of struts forming a substantially cylindrical outer body comprising a plurality of cells having two or more different shapes, a length of the outer body at least partially surrounding and substantially aligned with a length of the inner body; and a spring affixed proximate to a distal end of the pull wire, the spring having a compressed configuration and an elongated configuration, wherein in the clot engaging configuration, the inner body is configured to move proximally from a first position to a second position in relation to the outer body such that the spring transitions from the compressed configuration to the elongated configuration and at least a portion of the clot is compressed between the plurality of cells of the inner body and the plurality of cells of the outer body.

14. The clot retrieval device of claim 13, wherein the outer expandable framework comprises a plurality of clot reception spaces configured to pinch the clot between the inner body and the outer body when the inner body moves from the first position to the second position.

15. A method of capturing a clot, the method comprising:
deploying a clot retrieval device proximate to the clot, the clot retrieval device comprising:

a first expandable framework comprising a closed distal end, a closed proximal end, and a first plurality of struts forming a substantially cylindrical body comprising a plurality of cells having two or more different shapes;

a second expandable framework comprising a closed distal end, a closed proximal end, and a second plurality of struts forming a second substantially cylindrical body comprising a plurality of cells having two or more different shapes, a length of the second body at least partially surrounding and substantially aligned with a length of the first body; and a third expandable framework comprising a third plurality of struts forming a third body, the first body and the second body at least partially surrounding the third body in a clot engaging configuration, the third body configured to move in relation to the first body and the second body;

moving the first body proximally in the clot engaging configuration in relation to the second body to pinch at least a portion of the clot between the plurality of cells of the first body and the plurality of cells of the second body; and capturing one or more fragments of the clot.

16. The method of claim 15, wherein moving the first body in relation to the second body to pinch at least a portion of the clot between the first body and the second body includes applying tension to a pull wire, the pull wire being in mechanical communication with the first body.

17. The method of claim 15, further comprising retracting the first body and the second body simultaneously.

18. The method of claim 15, further comprising: retracting the third body in a proximal direction to engage the first body and the second body.

* * * * *